United States Patent
Teramoto et al.

(10) Patent No.: US 10,619,144 B2
(45) Date of Patent: Apr. 14, 2020

(54) REGULATED PEPC EXPRESSION

(71) Applicant: Novozymes A/S, Bagsvaerd (DK)

(72) Inventors: Hiroshi Teramoto, Ichikawa (JP);
Hiroaki Udagawa, Ichikawa (JP); Jan Lehmbeck, Veksø Sjælland (DK);
Michael Lynge Nielsen, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/913,967

(22) PCT Filed: Aug. 22, 2014

(86) PCT No.: PCT/EP2014/067949
§ 371 (c)(1),
(2) Date: Feb. 23, 2016

(87) PCT Pub. No.: WO2015/025055
PCT Pub. Date: Feb. 26, 2015

(65) Prior Publication Data
US 2016/0244737 A1    Aug. 25, 2016

(30) Foreign Application Priority Data
Aug. 23, 2013 (EP) .................................... 13181603

(51) Int. Cl.
| | |
|---|---|
| *C12N 9/62* | (2006.01) |
| *C12P 21/02* | (2006.01) |
| *C12N 9/18* | (2006.01) |
| *C12N 9/20* | (2006.01) |
| *C12N 9/82* | (2006.01) |
| *C12N 15/80* | (2006.01) |
| *C12N 9/02* | (2006.01) |
| *C12N 9/58* | (2006.01) |
| *C07K 14/38* | (2006.01) |

(52) U.S. Cl.
CPC .............. *C12N 9/62* (2013.01); *C07K 14/38* (2013.01); *C12N 9/0036* (2013.01); *C12N 9/18* (2013.01); *C12N 9/20* (2013.01); *C12N 9/58* (2013.01); *C12N 9/82* (2013.01); *C12N 15/80* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 6,025,185 | A | 2/2000 | Christensen et al. |
| 2004/0072325 | A1* | 4/2004 | Anazawa ............... C12N 15/80 |
| | | | 435/252.3 |
| 2004/0191864 | A1 | 9/2004 | Connelly et al. |
| 2012/0258489 | A1 | 10/2012 | Wenzel et al. |

FOREIGN PATENT DOCUMENTS

| | | | |
|---|---|---|---|
| EP | 0574347 A2 | 4/1993 | |
| WO | 1997022705 A1 | 6/1997 | |
| WO | WO 9722705 A1 * | 6/1997 | ............. C07K 14/38 |
| WO | 2006110677 A2 | 10/2006 | |
| WO | 2007045248 A1 | 4/2007 | |
| WO | 2008073914 A2 | 6/2008 | |
| WO | 2009071530 A1 | 6/2009 | |
| WO | 2011075677 A2 | 6/2011 | |

OTHER PUBLICATIONS

Meyer, Biotechnology Advances, 2008, vol. 26, pp. 177-185.*
Koivistoinen et al., FEBS Letters, 2012, vol. 586, pp. 378-383.*
deVries et al., Microbiology, and Molecular Biology Reviews, 2001, vol. 65 (4), pp. 497-522.*
Aspergillus oryzae RIB40, downloaded on Sep. 29, 2016 from: https://www.ncbi.nlm.nih.gov/protein/bae63304.*
Paoletti et al, 2001, Curr Genet 39(4), 244-252.
Reichard et al, 2000, Int J Med Microbiol 290 (6), 549-558.
Sharma et al, 2009, W J Microbiol Biotechnol 25(12), 2083-2094.
Yoon et al, 2011, Appl Microbiol Biotechnol 89(3), 747-759.
Kitamoto et al, 2008, Genbank accession No. D49701.
Machida et al, 2011, Genbank accession No. AP007167_Part 1.
Machida et al, 2011, Genbank accession No. AP007167_Part 2.
Takasaki et al, 2004, Biosci biotechnol biochem 68(4), 978-980.
Frederick et al, 2013, Genbank accession No. P33295.
Gouka et al, 1996, Appl Microbiol Biotechnol 46(1), 28-35.
Muller et al, 2002, Microbiology 148(12), 4025-4033.
Nierman et al, 2008, GenBank accession No. XP_753718.
Nierman, 2008, NCBI reference sequence No. XP_001259769.
Waring et al, 1989, Gene 79(1), 119-130.

* cited by examiner

*Primary Examiner* — Mindy G Brown
(74) *Attorney, Agent, or Firm* — Eric Fechter

(57) ABSTRACT

The present invention relates to a recombinant fungal host cell comprising at least one first polynucleotide encoding a polypeptide of interest; and one or more second polynucleotide encoding a fungal PepC protease, wherein the one or more second polynucleotide is operably linked to a regulated heterologous promoter, as well as a method for producing a polypeptide of interest, comprising cultivating said fungal host cell.

26 Claims, 3 Drawing Sheets

Specification includes a Sequence Listing.

SEQUENCE LISTING

```
<160> NUMBER OF SEQ ID NOS: 58

<210> SEQ ID NO 1
<211> LENGTH: 1485
<212> TYPE: DNA
<213> ORGANISM: Aspergillus oryzae
<220> FEATURE:
<221> NAME/KEY: CDS
<222> LOCATION: (1)..(1485)
<223> OTHER INFORMATION: PepC protease encoding sequence
<220> FEATURE:
<221> NAME/KEY: sig_peptide
<222> LOCATION: (1)..(48)
<220> FEATURE:
<221> NAME/KEY: misc_feature
<222> LOCATION: (49)..(345)
<223> OTHER INFORMATION: Pro-peptide
<220> FEATURE:
<221> NAME/KEY: mat_peptide
<222> LOCATION: (346)..(1485)
```

<400> SEQUENCE: 1

```
atg aga ggc atc ctc ggc ctt tcc ctg ctg cca cta cta gca gcg         45
Met Arg Gly Ile Leu Gly Leu Ser Leu Leu Pro Leu Leu Ala Ala
-115            -110                -105 gcc tcc ccc gtt gct gtt gac tcc atc cac aac gga gcg gct ccc att     93
Ala Ser Pro Val Ala Val Asp Ser Ile His Asn Gly Ala Ala Pro Ile
-100                -95                -90                 -85 ctt tcg gcc tca aat gcc aaa gag gtt cca gac tct tac att gtc gtc   141
Leu Ser Ala Ser Asn Ala Lys Glu Val Pro Asp Ser Tyr Ile Val Val
                -80              -75                  -70 ttc aag aag cat gtt tcc gct gaa acg gct gct gct cat cac acc tgg   189
Phe Lys Lys His Val Ser Ala Glu Thr Ala Ala Ala His His Thr Trp
            -65                  -60                  -55 gtg cag gac atc cac gat tcg atg act gga cgc atc gac ctg aag aag   237
Val Gln Asp Ile His Asp Ser Met Thr Gly Arg Ile Asp Leu Lys Lys
        -50                  -45                  -40 cgc tct ctt ttt ggt ttc agt gat gac ctt tac ctc ggt ctc aag aac   285
Arg Ser Leu Phe Gly Phe Ser Asp Asp Leu Tyr Leu Gly Leu Lys Asn
    -35                  -30                  -25 acc ttc gat atc gcc ggg tcc cta gcg ggc tac tcc gga cat ttc cat   333
Thr Phe Asp Ile Ala Gly Ser Leu Ala Gly Tyr Ser Gly His Phe His
-20                  -15                  -10                  -5 gag gat gtg atc gag cag gtc cgg aga cat cct gat gtt gaa tac atc   381
Glu Asp Val Ile Glu Gln Val Arg Arg His Pro Asp Val Glu Tyr Ile
        -1  1                    5                  10 gag aaa gac acc gaa gtc cac acc atg gag gag aca acc gag aag aat   429
Glu Lys Asp Thr Glu Val His Thr Met Glu Glu Thr Thr Glu Lys Asn
        15                  20                  25 gct ccc tgg ggc ttg gct cgt atc tct cac cgt gac agc ctc tcg ttc   477
Ala Pro Trp Gly Leu Ala Arg Ile Ser His Arg Asp Ser Leu Ser Phe
30                  35                  40 ggt acc ttt aac aag tac ctg tat gct tcg gaa ggc ggt gag ggt gtc   525
Gly Thr Phe Asn Lys Tyr Leu Tyr Ala Ser Glu Gly Gly Glu Gly Val
45                  50                  55                  60 gat gct tat act att gac act ggt atc aac att gag cat gtc gat ttc   573
Asp Ala Tyr Thr Ile Asp Thr Gly Ile Asn Ile Glu His Val Asp Phe
                65                  70                  75 gag gat cga gca cac tgg gga aag acc atc cct agc aat gat gag gat   621
Glu Asp Arg Ala His Trp Gly Lys Thr Ile Pro Ser Asn Asp Glu Asp
            80                  85                  90 gcg gat ggc aac gga cac gga act cac tgc tcc gga acc att gct ggt   669
Ala Asp Gly Asn Gly His Gly Thr His Cys Ser Gly Thr Ile Ala Gly
        95                  100                 105 aag aag tac ggt gtt gcc aag aag gcc aac atc tat gcc gtc aag gtc   717
Lys Lys Tyr Gly Val Ala Lys Lys Ala Asn Ile Tyr Ala Val Lys Val
    110                 115                 120 ttg agg tcc agc ggt tct ggc act atg tcc gat gtc gtt ctg ggt gtc   765
Leu Arg Ser Ser Gly Ser Gly Thr Met Ser Asp Val Val Leu Gly Val
125                 130                 135                 140 gag tgg gcc gtc cag tcc cac ctc aag aag gct aag gac gcc aaa gat   813
Glu Trp Ala Val Gln Ser His Leu Lys Lys Ala Lys Asp Ala Lys Asp
                145                 150                 155 gcc aag gtc aag ggt ttc aag ggc agc gtt gcc aac atg agt ctt ggt   861
Ala Lys Val Lys Gly Phe Lys Gly Ser Val Ala Asn Met Ser Leu Gly
            160                 165                 170 ggt gcc aag tcc agg acc ctt gag gct gct gtc aat gct ggt gtt gag   909
Gly Ala Lys Ser Arg Thr Leu Glu Ala Ala Val Asn Ala Gly Val Glu
        175                 180                 185 gct ggt ctt cac ttc gcc gtt gct gct ggt aac gac aat gcc gat gcc   957
Ala Gly Leu His Phe Ala Val Ala Ala Gly Asn Asp Asn Ala Asp Ala
```

```
Ala Gly Leu His Phe Ala Val Ala Ala Gly Asn Asp Asn Ala Asp Ala
        190                 195                 200 tgc aac tac tcc cct gct gcc gct gag aat gcc atc act gtc ggt gcc      1005
Cys Asn Tyr Ser Pro Ala Ala Ala Glu Asn Ala Ile Thr Val Gly Ala
205                 210                 215                 220 tcg acc ctt cag gat gag cgt gct tac ttc tcc aac tac gga aag tgc      1053
Ser Thr Leu Gln Asp Glu Arg Ala Tyr Phe Ser Asn Tyr Gly Lys Cys
                225                 230                 235 act gac atc ttt gcc ccg ggt ccc aac att ctt tcc acc tgg act ggc      1101
Thr Asp Ile Phe Ala Pro Gly Pro Asn Ile Leu Ser Thr Trp Thr Gly
            240                 245                 250 agc aag cac gct gtc aac acc atc tct gga acc tct atg gct tct cct      1149
Ser Lys His Ala Val Asn Thr Ile Ser Gly Thr Ser Met Ala Ser Pro
        255                 260                 265 cac att gct ggt ctg ctg gcc tac ttc gtt tct ctg cag cct gct cag      1197
His Ile Ala Gly Leu Leu Ala Tyr Phe Val Ser Leu Gln Pro Ala Gln
    270                 275                 280 gac tct gct ttc gct gtc gat gag ctt act cct gcc aag ctc aag aag      1245
Asp Ser Ala Phe Ala Val Asp Glu Leu Thr Pro Ala Lys Leu Lys Lys
285                 290                 295                 300 gat atc atc tcc atc gcc acc cag ggt gcc ctt act gat atc cca tct      1293
Asp Ile Ile Ser Ile Ala Thr Gln Gly Ala Leu Thr Asp Ile Pro Ser
                305                 310                 315 gac acc ccc aac ctt ctc gcc tgg aac ggc ggt ggt gcc gac aac tac      1341
Asp Thr Pro Asn Leu Leu Ala Trp Asn Gly Gly Gly Ala Asp Asn Tyr
            320                 325                 330 acc cag att gtc gcc aag ggt gga tac aag gcc ggc agt gac aac ctt      1389
Thr Gln Ile Val Ala Lys Gly Gly Tyr Lys Ala Gly Ser Asp Asn Leu
        335                 340                 345 aag gac cgc ttt gac gga cta gtc aac aag gcc gag aag ttg ctc gct      1437
Lys Asp Arg Phe Asp Gly Leu Val Asn Lys Ala Glu Lys Leu Leu Ala
    350                 355                 360 gag gag ctt gga gct att tac agt gag atc cag ggt gct gtt gtt gca      1485
Glu Glu Leu Gly Ala Ile Tyr Ser Glu Ile Gln Gly Ala Val Val Ala
365                 370                 375                 380

<210> SEQ ID NO 2
<211> LENGTH: 495
<212> TYPE: PRT
<213> ORGANISM: Aspergillus oryzae

<400> SEQUENCE: 2

Met  Arg Gly Ile Leu Gly Leu Ser Leu Leu Pro  Leu Leu Ala Ala
-115               -110                -105

Ala  Ser Pro Val Ala Val Asp Ser Ile His Asn Gly Ala Ala Pro Ile
-100               -95                 -90                 -85

Leu Ser Ala Ser Asn Ala Lys Glu Val Pro Asp Ser Tyr Ile Val Val
                -80                 -75                 -70

Phe Lys Lys His Val Ser Ala Glu Thr Ala Ala Ala His His Thr Trp
            -65                 -60                 -55

Val Gln Asp Ile His Asp Ser Met Thr Gly Arg Ile Asp Leu Lys Lys
        -50                 -45                 -40

Arg Ser Leu Phe Gly Phe Ser Asp Asp Leu Tyr Leu Gly Leu Lys Asn
    -35                 -30                 -25

Thr Phe Asp Ile Ala Gly Ser Leu Ala Gly Tyr Ser Gly His Phe His
-20                 -15                 -10                 -5

Glu Asp Val Ile Glu Gln Val Arg Arg His Pro Asp Val Glu Tyr Ile
        -1  1                 5                   10
```

Glu Lys Asp Thr Glu Val His Thr Met Glu Thr Thr Glu Lys Asn
 15                  20                  25

Ala Pro Trp Gly Leu Ala Arg Ile Ser His Arg Asp Ser Leu Ser Phe
 30                  35                  40

Gly Thr Phe Asn Lys Tyr Leu Tyr Ala Ser Glu Gly Glu Gly Val
 45                  50                  55                  60

Asp Ala Tyr Thr Ile Asp Thr Gly Ile Asn Ile Glu His Val Asp Phe
                     65                  70                  75

Glu Asp Arg Ala His Trp Gly Lys Thr Ile Pro Ser Asn Asp Glu Asp
                 80                  85                  90

Ala Asp Gly Asn Gly His Gly Thr His Cys Ser Gly Thr Ile Ala Gly
             95                 100                 105

Lys Lys Tyr Gly Val Ala Lys Lys Ala Asn Ile Tyr Ala Val Lys Val
        110                 115                 120

Leu Arg Ser Ser Gly Ser Gly Thr Met Ser Asp Val Val Leu Gly Val
125                 130                 135                 140

Glu Trp Ala Val Gln Ser His Leu Lys Lys Ala Lys Asp Ala Lys Asp
                    145                 150                 155

Ala Lys Val Lys Gly Phe Lys Gly Ser Val Ala Asn Met Ser Leu Gly
                160                 165                 170

Gly Ala Lys Ser Arg Thr Leu Glu Ala Ala Val Asn Ala Gly Val Glu
            175                 180                 185

Ala Gly Leu His Phe Ala Val Ala Ala Gly Asn Asp Asn Ala Asp Ala
        190                 195                 200

Cys Asn Tyr Ser Pro Ala Ala Ala Glu Asn Ala Ile Thr Val Gly Ala
205                 210                 215                 220

Ser Thr Leu Gln Asp Glu Arg Ala Tyr Phe Ser Asn Tyr Gly Lys Cys
                    225                 230                 235

Thr Asp Ile Phe Ala Pro Gly Pro Asn Ile Leu Ser Thr Trp Thr Gly
                240                 245                 250

Ser Lys His Ala Val Asn Thr Ile Ser Gly Thr Ser Met Ala Ser Pro
            255                 260                 265

His Ile Ala Gly Leu Leu Ala Tyr Phe Val Ser Leu Gln Pro Ala Gln
        270                 275                 280

Asp Ser Ala Phe Ala Val Asp Glu Leu Thr Pro Ala Lys Leu Lys Lys
285                 290                 295                 300

Asp Ile Ile Ser Ile Ala Thr Gln Gly Ala Leu Thr Asp Ile Pro Ser
                    305                 310                 315

Asp Thr Pro Asn Leu Leu Ala Trp Asn Gly Gly Ala Asp Asn Tyr
                320                 325                 330

Thr Gln Ile Val Ala Lys Gly Gly Tyr Lys Ala Gly Ser Asp Asn Leu
            335                 340                 345

Lys Asp Arg Phe Asp Gly Leu Val Asn Lys Ala Glu Lys Leu Leu Ala
350                 355                 360

Glu Glu Leu Gly Ala Ile Tyr Ser Glu Ile Gln Gly Ala Val Val Ala
365                 370                 375                 380

<210> SEQ ID NO 3
<211> LENGTH: 1599
<212> TYPE: DNA
<213> ORGANISM: Aspergillus niger
<220> FEATURE:
<221> NAME/KEY: CDS
<222> LOCATION: (1)..(1599)
<223> OTHER INFORMATION: PepC protease encoding sequence
<220> FEATURE:

```
<221> NAME/KEY: sig_peptide
<222> LOCATION: (1)..(48)
<220> FEATURE:
<221> NAME/KEY: misc_feature
<222> LOCATION: (49)..(345)
<223> OTHER INFORMATION: Pro-peptide
<220> FEATURE:
<221> NAME/KEY: mat_peptide
<222> LOCATION: (346)..(1599)

<400> SEQUENCE: 3
```

| | | | | | | | | | | | | | | | | |
|---|---|---|---|---|---|---|---|---|---|---|---|---|---|---|---|---|
| atg | aag | ggc | atc | ctc | ggc | ctt | tcc | ctc | ctc | ccg | ttg | ctg | acg | gct | | 45 |
| Met | Lys | Gly | Ile | Leu | Gly | Leu | Ser | Leu | Leu | Pro | Leu | Leu | Thr | Ala | | |
| -115 | | | | -110 | | | | | -105 | | | | | | | |
| gcg | tcg | ccc | gtc | ttc | gtt | gac | tcc | atc | cat | aat | gaa | gct | gcc | ccc | atc | 93 |
| Ala | Ser | Pro | Val | Phe | Val | Asp | Ser | Ile | His | Asn | Glu | Ala | Ala | Pro | Ile | |
| -100 | | | | | -95 | | | | | -90 | | | | | -85 | |
| ttg | tct | gct | acc | aac | gcg | aag | gag | gtt | ccc | gac | tcc | tac | atc | gtc | gtt | 141 |
| Leu | Ser | Ala | Thr | Asn | Ala | Lys | Glu | Val | Pro | Asp | Ser | Tyr | Ile | Val | Val | |
| | | | | -80 | | | | | -75 | | | | | -70 | | |
| ttc | aag | aag | cac | gtc | act | tca | gag | ctg | gct | tcg | gct | cac | cac | agc | tgg | 189 |
| Phe | Lys | Lys | His | Val | Thr | Ser | Glu | Leu | Ala | Ser | Ala | His | His | Ser | Trp | |
| | | -65 | | | | | -60 | | | | | -55 | | | | |
| gtg | cag | gac | atc | cat | gac | tct | cag | agc | gag | cgg | act | gag | ctg | aag | aag | 237 |
| Val | Gln | Asp | Ile | His | Asp | Ser | Gln | Ser | Glu | Arg | Thr | Glu | Leu | Lys | Lys | |
| | -50 | | | | | -45 | | | | | -40 | | | | | |
| cgg | tcg | ctc | ttc | ggc | ctt | ggg | gac | gag | gtc | tat | ctg | ggt | ctc | aag | aac | 285 |
| Arg | Ser | Leu | Phe | Gly | Leu | Gly | Asp | Glu | Val | Tyr | Leu | Gly | Leu | Lys | Asn | |
| -35 | | | | | -30 | | | | | -25 | | | | | | |
| acc | ttt | gac | att | gct | ggt | tct | ctg | atc | ggt | tac | tct | ggt | cac | ttc | cac | 333 |
| Thr | Phe | Asp | Ile | Ala | Gly | Ser | Leu | Ile | Gly | Tyr | Ser | Gly | His | Phe | His | |
| -20 | | | | | -15 | | | | | -10 | | | | | -5 | |
| gag | gat | gtc | atc | gag | caa | gtc | cgc | aga | cac | ccc | gat | gtc | gat | tac | atc | 381 |
| Glu | Asp | Val | Ile | Glu | Gln | Val | Arg | Arg | His | Pro | Asp | Val | Asp | Tyr | Ile | |
| | | | -1 | 1 | | | | 5 | | | | | 10 | | | |
| gag | cgg | gat | tcc | gaa | gtt | cac | acc | atg | gaa | ggg | gcc | acc | gaa | aag | aac | 429 |
| Glu | Arg | Asp | Ser | Glu | Val | His | Thr | Met | Glu | Gly | Ala | Thr | Glu | Lys | Asn | |
| | | 15 | | | | | 20 | | | | | 25 | | | | |
| gcc | cct | tgg | ggt | ctg | gct | cgt | atc | tct | cac | cgt | gat | agc | ctg | acc | ttc | 477 |
| Ala | Pro | Trp | Gly | Leu | Ala | Arg | Ile | Ser | His | Arg | Asp | Ser | Leu | Thr | Phe | |
| 30 | | | | | 35 | | | | | 40 | | | | | | |
| ggt | aac | ttc | aac | aag | tac | ctg | tat | gcc | tcc | gag | ggg | ggt | gag | ggc | gtt | 525 |
| Gly | Asn | Phe | Asn | Lys | Tyr | Leu | Tyr | Ala | Ser | Glu | Gly | Gly | Glu | Gly | Val | |
| 45 | | | | 50 | | | | | 55 | | | | | 60 | | |
| gac | gcc | tac | acc | att | gac | acg | ggt | atc | aac | gtt | gac | cac | gtt | gac | ttc | 573 |
| Asp | Ala | Tyr | Thr | Ile | Asp | Thr | Gly | Ile | Asn | Val | Asp | His | Val | Asp | Phe | |
| | | | 65 | | | | | 70 | | | | | 75 | | | |
| gag | ggc | cgt | gcc | act | tgg | ggc | aag | aca | atc | cct | acc | aac | gat | gaa | gat | 621 |
| Glu | Gly | Arg | Ala | Thr | Trp | Gly | Lys | Thr | Ile | Pro | Thr | Asn | Asp | Glu | Asp | |
| | | | 80 | | | | | 85 | | | | | 90 | | | |
| ctc | gat | ggc | aat | ggt | cac | gga | act | cac | tgc | tcc | gga | acc | atg | gct | ggt | 669 |
| Leu | Asp | Gly | Asn | Gly | His | Gly | Thr | His | Cys | Ser | Gly | Thr | Met | Ala | Gly | |
| | | 95 | | | | | 100 | | | | | 105 | | | | |
| aag | aag | tac | ggt | gtt | gcc | aag | aag | gcc | aac | ctc | tat | gct | gtc | aag | gtc | 717 |
| Lys | Lys | Tyr | Gly | Val | Ala | Lys | Lys | Ala | Asn | Leu | Tyr | Ala | Val | Lys | Val | |
| | 110 | | | | | 115 | | | | | 120 | | | | | |
| ctc | cgg | tcg | agc | ggc | tct | ggc | acc | atg | tct | gat | gtc | gtt | tct | ggt | gtc | 765 |
| Leu | Arg | Ser | Ser | Gly | Ser | Gly | Thr | Met | Ser | Asp | Val | Val | Ser | Gly | Val | |
| 125 | | | | | 130 | | | | | 135 | | | | | 140 | |
| gag | tat | gcc | gtc | cag | gct | cat | atc | aag | aag | gcc | aag | gat | gcc | aag | aac | 813 |
| Glu | Tyr | Ala | Val | Gln | Ala | His | Ile | Lys | Lys | Ala | Lys | Asp | Ala | Lys | Asn | |
| | | | 145 | | | | | 150 | | | | | 155 | | | |

```
ggc aag gtc aag gga ttc aag ggc agc gtt gcc aac atg agt ctc ggt      861
Gly Lys Val Lys Gly Phe Lys Gly Ser Val Ala Asn Met Ser Leu Gly
        160                 165                 170 ggt ggc aag tct aag acc ctc gag gat gct gtt aac gct ggt gtt gag      909
Gly Gly Lys Ser Lys Thr Leu Glu Asp Ala Val Asn Ala Gly Val Glu
    175                 180                 185 gct ggt ctt cac ttc gcc gtt gcc gcc ggt aat gac aat gct gat gct      957
Ala Gly Leu His Phe Ala Val Ala Ala Gly Asn Asp Asn Ala Asp Ala
190                 195                 200 tgc aac tac tct cct gct gct gcc gag aag gcc atc acc gtt ggt gcc     1005
Cys Asn Tyr Ser Pro Ala Ala Ala Glu Lys Ala Ile Thr Val Gly Ala
205                 210                 215                 220 tcg aca ctt gct gac gag cgt gcg tac ttc tcc aac tac gga gag tgc     1053
Ser Thr Leu Ala Asp Glu Arg Ala Tyr Phe Ser Asn Tyr Gly Glu Cys
                225                 230                 235 act gac atc ttc gct cct ggt ctc aac atc ctg tcc acc tgg att ggc     1101
Thr Asp Ile Phe Ala Pro Gly Leu Asn Ile Leu Ser Thr Trp Ile Gly
            240                 245                 250 agc aac tac gcc acc aac atc atc tct ggc act tcc atg gcc tct cct     1149
Ser Asn Tyr Ala Thr Asn Ile Ile Ser Gly Thr Ser Met Ala Ser Pro
        255                 260                 265 cac att gct ggc ctg ctg gcc tac ttt gtc tcc ctc cag ccc ccc tcg     1197
His Ile Ala Gly Leu Leu Ala Tyr Phe Val Ser Leu Gln Pro Pro Ser
    270                 275                 280 gac tct gca ttc gct gtt gag gag ctt act cct gct aag ctg aag aag     1245
Asp Ser Ala Phe Ala Val Glu Glu Leu Thr Pro Ala Lys Leu Lys Lys
285                 290                 295                 300 gac atc atc gcc atc gcc acc gag ggc gct ctc act gac att ccc tcc     1293
Asp Ile Ile Ala Ile Ala Thr Glu Gly Ala Leu Thr Asp Ile Pro Ser
                305                 310                 315 aac acc ccc aac gta agt cat gcc gct gtt ggt att tat aag aga aac     1341
Asn Thr Pro Asn Val Ser His Ala Ala Val Gly Ile Tyr Lys Arg Asn
            320                 325                 330 gag cta act cag aaa ttc agc tcc ttg cct gga acg gtg gtg gtt ccg     1389
Glu Leu Thr Gln Lys Phe Ser Ser Leu Pro Gly Thr Val Val Val Pro
        335                 340                 345 aga act aca ccg aca tcg ttg gca gcg gtg gct aca agg tct cct ctg     1437
Arg Thr Thr Pro Thr Ser Leu Ala Ala Val Ala Thr Arg Ser Pro Leu
    350                 355                 360 cca aga acc gca tcg agg acc gta ttg agg gtc tcg ttc aca agg ccg     1485
Pro Arg Thr Ala Ser Arg Thr Val Leu Arg Val Ser Phe Thr Arg Pro
365                 370                 375                 380 aag agc tgc tca ccg agg agc ttg gtg cca tct aca gcg aga tcc agg     1533
Lys Ser Cys Ser Pro Arg Ser Leu Val Pro Ser Thr Ala Arg Ser Arg
                385                 390                 395 atg ccg tcg tcg cat aga tca gaa ctc gtg ctt tcc aga ctt aga tcg     1581
Met Pro Ser Ser His Arg Ser Glu Leu Val Leu Ser Arg Leu Arg Ser
            400                 405                 410 gaa gac ttg gtt ttt ttt                                             1599
Glu Asp Leu Val Phe Phe
        415
```

<210> SEQ ID NO 4
<211> LENGTH: 533
<212> TYPE: PRT
<213> ORGANISM: Aspergillus niger

<400> SEQUENCE: 4

```
Met  Lys Gly Ile Leu Gly  Leu Ser Leu Leu Pro  Leu Leu Thr Ala
-115                 -110                 -105
```

```
Ala Ser Pro Val Phe Val Asp Ser Ile His Asn Glu Ala Ala Pro Ile
-100            -95                 -90             -85

Leu Ser Ala Thr Asn Ala Lys Glu Val Pro Asp Ser Tyr Ile Val Val
            -80                 -75                 -70

Phe Lys Lys His Val Thr Ser Glu Leu Ala Ser Ala His His Ser Trp
        -65                 -60                 -55

Val Gln Asp Ile His Asp Ser Gln Ser Glu Arg Thr Glu Leu Lys Lys
    -50                 -45                 -40

Arg Ser Leu Phe Gly Leu Gly Asp Glu Val Tyr Leu Gly Leu Lys Asn
-35                 -30                 -25

Thr Phe Asp Ile Ala Gly Ser Leu Ile Gly Tyr Ser Gly His Phe His
-20             -15                 -10                     -5

Glu Asp Val Ile Glu Gln Val Arg Arg His Pro Asp Val Asp Tyr Ile
        -1  1               5                   10

Glu Arg Asp Ser Glu Val His Thr Met Glu Gly Ala Thr Glu Lys Asn
            15                  20                  25

Ala Pro Trp Gly Leu Ala Arg Ile Ser His Arg Asp Ser Leu Thr Phe
            30                  35                  40

Gly Asn Phe Asn Lys Tyr Leu Tyr Ala Ser Glu Gly Glu Gly Val
45                  50                  55                  60

Asp Ala Tyr Thr Ile Asp Thr Gly Ile Asn Val Asp His Val Asp Phe
                65                  70                  75

Glu Gly Arg Ala Thr Trp Gly Lys Thr Ile Pro Thr Asn Asp Glu Asp
            80                  85                  90

Leu Asp Gly Asn Gly His Gly Thr His Cys Ser Gly Thr Met Ala Gly
            95                  100                 105

Lys Lys Tyr Gly Val Ala Lys Lys Ala Asn Leu Tyr Ala Val Lys Val
    110                 115                 120

Leu Arg Ser Ser Gly Ser Gly Thr Met Ser Asp Val Val Ser Gly Val
125                 130                 135                 140

Glu Tyr Ala Val Gln Ala His Ile Lys Lys Ala Lys Asp Ala Lys Asn
                145                 150                 155

Gly Lys Val Lys Gly Phe Lys Gly Ser Val Ala Asn Met Ser Leu Gly
            160                 165                 170

Gly Gly Lys Ser Lys Thr Leu Glu Asp Ala Val Asn Ala Gly Val Glu
        175                 180                 185

Ala Gly Leu His Phe Ala Val Ala Ala Gly Asn Asp Asn Ala Asp Ala
        190                 195                 200

Cys Asn Tyr Ser Pro Ala Ala Ala Glu Lys Ala Ile Thr Val Gly Ala
205                 210                 215                 220

Ser Thr Leu Ala Asp Glu Arg Ala Tyr Phe Ser Asn Tyr Gly Glu Cys
                225                 230                 235

Thr Asp Ile Phe Ala Pro Gly Leu Asn Ile Leu Ser Thr Trp Ile Gly
            240                 245                 250

Ser Asn Tyr Ala Thr Asn Ile Ile Ser Gly Thr Ser Met Ala Ser Pro
        255                 260                 265

His Ile Ala Gly Leu Leu Ala Tyr Phe Val Ser Leu Gln Pro Pro Ser
    270                 275                 280

Asp Ser Ala Phe Ala Val Glu Glu Leu Thr Pro Ala Lys Leu Lys Lys
285                 290                 295                 300

Asp Ile Ile Ala Ile Ala Thr Glu Gly Ala Leu Thr Asp Ile Pro Ser
                305                 310                 315
```

```
Asn Thr Pro Asn Val Ser His Ala Ala Val Gly Ile Tyr Lys Arg Asn
            320                 325                 330

Glu Leu Thr Gln Lys Phe Ser Ser Leu Pro Gly Thr Val Val Val Pro
        335                 340                 345

Arg Thr Thr Pro Thr Ser Leu Ala Ala Val Ala Thr Arg Ser Pro Leu
    350                 355                 360

Pro Arg Thr Ala Ser Arg Thr Val Leu Arg Val Ser Phe Thr Arg Pro
365                 370                 375                 380

Lys Ser Cys Ser Pro Arg Ser Leu Val Pro Ser Thr Ala Arg Ser Arg
            385                 390                 395

Met Pro Ser Ser His Arg Ser Glu Leu Val Leu Ser Arg Leu Arg Ser
            400                 405                 410

Glu Asp Leu Val Phe Phe
        415
```

<210> SEQ ID NO 5
<211> LENGTH: 19
<212> TYPE: DNA
<213> ORGANISM: artificial sequence
<220> FEATURE:
<223> OTHER INFORMATION: Primer oJaL113

<400> SEQUENCE: 5
gagctgctgg atttggctg                                             19

<210> SEQ ID NO 6
<211> LENGTH: 19
<212> TYPE: DNA
<213> ORGANISM: artificial sequence
<220> FEATURE:
<223> OTHER INFORMATION: Primer oJaL114

<400> SEQUENCE: 6
ccaacagccg actcaggag                                             19

<210> SEQ ID NO 7
<211> LENGTH: 19
<212> TYPE: DNA
<213> ORGANISM: artificial sequence
<220> FEATURE:
<223> OTHER INFORMATION: Primer oJaL228

<400> SEQUENCE: 7
accagcagca acggcgaag                                             19

<210> SEQ ID NO 8
<211> LENGTH: 38
<212> TYPE: DNA
<213> ORGANISM: artificial sequence
<220> FEATURE:
<223> OTHER INFORMATION: Primer oJaL229

<400> SEQUENCE: 8
ggccttccct gccggtaaca tgagaggcat cctcggcc                        38

<210> SEQ ID NO 9
<211> LENGTH: 38
<212> TYPE: DNA
<213> ORGANISM: artificial sequence
<220> FEATURE:
<223> OTHER INFORMATION: Primer oJaL230

<400> SEQUENCE: 9
ggccgaggat gcctctcatg ttaccggcag ggaaggcc                                   38

<210> SEQ ID NO 10
<211> LENGTH: 40
<212> TYPE: DNA
<213> ORGANISM: artificial sequence
<220> FEATURE:
<223> OTHER INFORMATION: Primer oJaL231

<400> SEQUENCE: 10
cgtccacgcg gggattatgc ggatgtggac gggttatcgg                                 40

<210> SEQ ID NO 11
<211> LENGTH: 40
<212> TYPE: DNA
<213> ORGANISM: artificial sequence
<220> FEATURE:
<223> OTHER INFORMATION: Primer oJaL232

<400> SEQUENCE: 11
ccgataaccc gtccacatcc gcataatccc cgcgtggacg                                 40

<210> SEQ ID NO 12
<211> LENGTH: 40
<212> TYPE: DNA
<213> ORGANISM: artificial sequence
<220> FEATURE:
<223> OTHER INFORMATION: Primer oJaL233

<400> SEQUENCE: 12
taatcactcc gaaaggtccc ccccgtcaag gagcttatcg                                 40

<210> SEQ ID NO 13
<211> LENGTH: 40
<212> TYPE: DNA
<213> ORGANISM: artificial sequence
<220> FEATURE:
<223> OTHER INFORMATION: Primer oJaL234

<400> SEQUENCE: 13
cgataagctc cttgacgggg gggacctttc ggagtgatta                                 40

<210> SEQ ID NO 14
<211> LENGTH: 18
<212> TYPE: DNA
<213> ORGANISM: artificial sequence
<220> FEATURE:
<223> OTHER INFORMATION: Primer oJaL235

<400> SEQUENCE: 14
gcacagccgt agtgggag                                                        18

<210> SEQ ID NO 15
<211> LENGTH: 27
<212> TYPE: DNA
<213> ORGANISM: artificial sequence
<220> FEATURE:
<223> OTHER INFORMATION: Primer B2103F03

<400> SEQUENCE: 15
actagttaga atgctggacc agccccg                                              27

<210> SEQ ID NO 16
<211> LENGTH: 23
<212> TYPE: DNA
<213> ORGANISM: artificial sequence
<220> FEATURE:
<223> OTHER INFORMATION: Primer B2103F04

<400> SEQUENCE: 16
aagcttattt gtctctgaca cac                                           23

<210> SEQ ID NO 17
<211> LENGTH: 46
<212> TYPE: DNA
<213> ORGANISM: artificial sequence
<220> FEATURE:
<223> OTHER INFORMATION: Primer P801

<400> SEQUENCE: 17
gaaacctgtc gtgccagtta attaagagag agttgaacct ggacgc                  46

<210> SEQ ID NO 18
<211> LENGTH: 46
<212> TYPE: DNA
<213> ORGANISM: artificial sequence
<220> FEATURE:
<223> OTHER INFORMATION: Primer P802

<400> SEQUENCE: 18
gcggccgctt tttttgcga tcgcggtgac tgacacctgg cggtag                   46

<210> SEQ ID NO 19
<211> LENGTH: 45
<212> TYPE: DNA
<213> ORGANISM: artificial sequence
<220> FEATURE:
<223> OTHER INFORMATION: Primer P803

<400> SEQUENCE: 19
gcgatcgcaa aaaaagcgg ccgcccccag ttgtgtatat agagg                    45

<210> SEQ ID NO 20
<211> LENGTH: 48
<212> TYPE: DNA
<213> ORGANISM: artificial sequence
<220> FEATURE:
<223> OTHER INFORMATION: Primer P804

<400> SEQUENCE: 20
gccgattcat taatgcaggg cgcgcctgaa tgtataagct agcttccg                48

<210> SEQ ID NO 21
<211> LENGTH: 47
<212> TYPE: DNA
<213> ORGANISM: artificial sequence
<220> FEATURE:
<223> OTHER INFORMATION: Primer P805

<400> SEQUENCE: 21
tagcttatac attcaggcgc gccttcggta aatacactat cacacac                 47

<210> SEQ ID NO 22
<211> LENGTH: 51
<212> TYPE: DNA
<213> ORGANISM: artificial sequence
<220> FEATURE:
<223> OTHER INFORMATION: Primer P806

<400> SEQUENCE: 22
gattcattaa tgcagggcgc ggtttaaaca ttagtgatac cccactctaa g            51

<210> SEQ ID NO 23
<211> LENGTH: 39
<212> TYPE: DNA
<213> ORGANISM: artificial sequence
<220> FEATURE:
<223> OTHER INFORMATION: Primer P830

<400> SEQUENCE: 23
aaaaaaggcc ttcttggccc cacacaacat acgagccgg                                  39

<210> SEQ ID NO 24
<211> LENGTH: 36
<212> TYPE: DNA
<213> ORGANISM: artificial sequence
<220> FEATURE:
<223> OTHER INFORMATION: Primer P831

<400> SEQUENCE: 24
aaaaaagctt ttatacattc aaatatgtat ccgctc                                     36

<210> SEQ ID NO 25
<211> LENGTH: 952
<212> TYPE: DNA
<213> ORGANISM: Humicola lanuginosa

<400> SEQUENCE: 25
gcggccgcac catgaagttc ttcaccacca tcctcagcac cgccagcctt gttgctgctc            60
tccccgccgc tgttgactcg aaccatacccc cggccgctcc tgaacttgtt gcccggagtc          120
ctattcgtcg agaggtctcg caggatctgt ttaaccagtt caatctcttt gcacagtatt          180
ctgcagccgc atactgcgga aaaaacaatg atgccccagc tggtacaaac attacgtgcc          240
gcggacgggc ctgccccgag gtagagaagg cggatgcaac gtttctctac tcgtttgaag          300
actctggagt gggcgatgtc accggcttcc ttgctctcga caacacgaac aaattgatcg          360
tcctctcttt ccgtggctct cgttccatag agaactggat cgcgaatctt aacttcggct          420
tgaaagaaat aaatgacatt tgctccggct gcaggggaca tgacggcttc acttcgtcct          480
ggaggtctgt agccgatacg ttaaggcaga aggtggagga tgctgtgagg gagcatcccg          540
actatcgcgt ggtgtttacc ggacatagct tgggtggtgc attggcaact gttgccggag          600
cagacctgcg tggaaatggg tatgatatcg acgtgttttc atatgcgcc ccccgagtcg           660 gaaacagggc ttttgcagaa ttcctgaccg tacagaccgg cggaacactc taccgcatta          720
cccacaccaa tgatattgtc cctagactcc cgccgcgcga attcggttac agccattcta          780
gcccagaata ctggatcaaa tctggaaccc ttgtccccgt ccggcgacga gacatcgtga          840
agatagaagg catcgatgcc accggcggca ataaccagcc taacattccg gatatccctg          900
cgcacctatg gtacttcggg ttaattggga catgtcttta gtaagcgatc gc                  952

<210> SEQ ID NO 26
<211> LENGTH: 20
<212> TYPE: DNA
<213> ORGANISM: artificial sequence
<220> FEATURE:
<223> OTHER INFORMATION: Primer P875

<400> SEQUENCE: 26
cagttgtcgc ttggtgcatc                                                       20

<210> SEQ ID NO 27
<211> LENGTH: 51

```
<212> TYPE: DNA
<213> ORGANISM: artificial sequence
<220> FEATURE:
<223> OTHER INFORMATION: Primer P882

<400> SEQUENCE: 27
cttagagtgg ggtatcacta ataagcttgt ttctgcatta atgaatcggc c                51

<210> SEQ ID NO 28
<211> LENGTH: 28
<212> TYPE: DNA
<213> ORGANISM: artificial sequence
<220> FEATURE:
<223> OTHER INFORMATION: Primer P881

<400> SEQUENCE: 28
aagcttatta gtgatacccc actctaag                                          28

<210> SEQ ID NO 29
<211> LENGTH: 21
<212> TYPE: DNA
<213> ORGANISM: artificial sequence
<220> FEATURE:
<223> OTHER INFORMATION: Primer P864

<400> SEQUENCE: 29
aggacttccc ctacggctcc g                                                 21

<210> SEQ ID NO 30
<211> LENGTH: 21
<212> TYPE: DNA
<213> ORGANISM: artificial sequence
<220> FEATURE:
<223> OTHER INFORMATION: Primer P200

<400> SEQUENCE: 30
ccaactccgc cgttgcatat c                                                 21

<210> SEQ ID NO 31
<211> LENGTH: 36
<212> TYPE: DNA
<213> ORGANISM: artificial sequence
<220> FEATURE:
<223> OTHER INFORMATION: Primer P920

<400> SEQUENCE: 31 tttttttttaa ttaattggcg gtgatattga tggcac                                36

<210> SEQ ID NO 32
<211> LENGTH: 48
<212> TYPE: DNA
<213> ORGANISM: artificial sequence
<220> FEATURE:
<223> OTHER INFORMATION: Primer P921

<400> SEQUENCE: 32
aaaaaagctt gcatgcacta gtttatacat tcaaatatgt atccgctc                    48

<210> SEQ ID NO 33
<211> LENGTH: 43
<212> TYPE: DNA
<213> ORGANISM: artificial sequence
<220> FEATURE:
<223> OTHER INFORMATION: Primer P922

<400> SEQUENCE: 33
```

```
tagtgcatgc cctagggtcg acttaagcaa ggatttt ctt aac            43
```

<210> SEQ ID NO 34
<211> LENGTH: 50
<212> TYPE: DNA
<213> ORGANISM: artificial sequence
<220> FEATURE:
<223> OTHER INFORMATION: Primer P923

<400> SEQUENCE: 34

```
cgaccctagg gcatgcacta gtctgtcaga ccaagtttac tcatatatac      50
```

<210> SEQ ID NO 35
<211> LENGTH: 45
<212> TYPE: DNA
<213> ORGANISM: artificial sequence
<220> FEATURE:
<223> OTHER INFORMATION: Primer P924

<400> SEQUENCE: 35

```
aaaaaagctt actagtgcat gcgtttctgc attaatgaat cggcc           45
```

<210> SEQ ID NO 36
<211> LENGTH: 42
<212> TYPE: DNA
<213> ORGANISM: artificial sequence
<220> FEATURE:
<223> OTHER INFORMATION: Primer MLxnoli20

<400> SEQUENCE: 36

```
caactggggg cggccgcacc atgaagctac tctctctgac cg              42
```

<210> SEQ ID NO 37
<211> LENGTH: 34
<212> TYPE: DNA
<213> ORGANISM: artificial sequence
<220> FEATURE:
<223> OTHER INFORMATION: Primer MLxnoli21

<400> SEQUENCE: 37

```
gtcagtcacc gcgatcgctc aggggg tgac gatg                      34
```

<210> SEQ ID NO 38
<211> LENGTH: 690
<212> TYPE: DNA
<213> ORGANISM: Humicola insolens

<400> SEQUENCE: 38

```
atgaagttct tcaccacgat cctctcgact gcctcgttgg tcgcagcctt gcctgcggca    60
gtggattcca accacacacc ggcagcaccc gagctcgtgg cacgccagct cggagccatc   120
cagaacgact ggaatcgggt tcgcctgac gcgtgtcccg atgcaattct catttt cgca   180
cgaggatcga tggaacccgg taacatgggt atcactgtcg acctgcgtt ggcaaacggt    240
ttgaaggagc atatccccaa catctggatt cagggagtgg gtggccctta cgacgcagcg   300
ctcgcaacca acttcttgcc tcgcggaacg tcgcaggcca catcgacga gggaaaaagg    360
ctcttccacc tcgcccatca gaagtgtccc aacacaccgg tggtggcagg aggatactcc   420
cagggtgcag cgttgattgc cgcagccgtc tcggaattgt cgggagcagt gaaggagcag   480
gtcaagggag tcgtcttgtt cggatacacc cagaacctcc agaaccgagg aggcattccc   540
aactatcctc gcgagcgcac gaaggtgttc tgtaacgtgg gtgatgccgt gtgtacaggc   600
atcccgatca tcactcctgc ccacctctcg tataccatcc aggcgagggg tgaggcagca   660
```

```
cggttcctcg tcgaccgaat tagggcgtga                                      690
```

<210> SEQ ID NO 39
<211> LENGTH: 47
<212> TYPE: DNA
<213> ORGANISM: artificial sequence
<220> FEATURE:
<223> OTHER INFORMATION: Primer DAuP810

<400> SEQUENCE: 39

```
caactggggg cggccgcacc atgaagttct tcaccacgat cctctcg                    47
```

<210> SEQ ID NO 40
<211> LENGTH: 41
<212> TYPE: DNA
<213> ORGANISM: artificial sequence
<220> FEATURE:
<223> OTHER INFORMATION: Primer DAuP811

<400> SEQUENCE: 40

```
gtcagtcacc gcgatcgtca cgccctaatt cggtcgacga g                          41
```

<210> SEQ ID NO 41
<211> LENGTH: 1400
<212> TYPE: DNA
<213> ORGANISM: Aspergillus oryzae
<220> FEATURE:
<221> NAME/KEY: promoter
<222> LOCATION: (1)..(1400)
<223> OTHER INFORMATION: Aspergillus oryzae niaD promoter, PniaD.

<400> SEQUENCE: 41

```
gttaccggca gggaaggcca atgaaagtaa aattacgagg gagggagcat gaacaaggat       60
gctgagtatg aataagtcga atggtcagcc agtgcattaa ctccaaataa ggaggcaatc      120
caccacacta aaatactctt gcctatcgta tgatggcacg cagtacgtgt tacccatgcg      180
cgggcagtgg acattctatt aggtcacggc agtaactcct tgttaccata taacgcctcg      240
gagaaaggtc acaataagca atgctcctag gaacccacca gcgatttccg cggagtccca      300
aaatcagctc attctgggag gtgggacgct cgaaattagg gcaagccttc aggctggacg      360
gcgtcccacc gcttaaccaa gcgttgaggc aaataaatcg cgttgaccca cacaacactc      420
tcgaggctcc agccatttgt ccgctcaacc ttgcaggatt tctttttcgt catattaatt      480
ggttctttga agaatgatgg agacaatgcc gtgaagccat gtgcaacttc caattagaag      540
tgttgttgct tatcgtccga atgagcctgg ttcgcgtgga gaatgggcca gatgggagct      600
cacggctgtt agagcggagc tactactctg tacgtaccct tcaaaggaat tctcggtaag      660
tttgttagag ggatattgct cacgtttaat tggcactcca ggatccttta aatccaggca      720
aaaatcgctc gatctggctt tttttgccaa tcttggaagt ctaccgtata cttgtagtta      780
cacccttgag gatttaccac atgagaagaa caccaaccta actgcgtgat taaaacgcc      840 attgctatga tgcttgaaga gtgccggata tatcggcatc taacttagga tttgtcttac      900
gtacaatatt tatgacctgt ggtgaaacct gaggcaacaa gggggcgcga tttaccagac      960
tggcgttcac ataccaatac agtgcttaat tgtaggtctc atgggtggaa tgagatgacc     1020
ttcccttcca tctattctta agaggaacag ggatggtacc cacaccatac cccgaagagc     1080
tcgtgatgta atagaccctt tcgtagtatg cgggttttta ttgagatgcc gatatgcaaa     1140
cttgtagtaa gactaataat aacaggtgca attaattgaa tttggggcct gttaagcttt     1200
```

```
tcgtccgacc accagtgacg tccgtccgat aagccgggaa cgatcgataa ggaggctatc   1260
ccgtcgatcc tgactaacct tttccagttg ttccttaact ttgcaccatc tccgcggagg   1320
aatccctgac ccaatcttat ggtgaggtgc tatcgtcctt atcaatccct gtcacgattg   1380
ccgataaccc gtccacatcc                                              1400

<210> SEQ ID NO 42
<211> LENGTH: 1400
<212> TYPE: DNA
<213> ORGANISM: Aspergillus oryzae
<220> FEATURE:
<221> NAME/KEY: promoter
<222> LOCATION: (1)..(1400)
<223> OTHER INFORMATION: Aspergillus oryzae sorA promoter, PsorA.

<400> SEQUENCE: 42
ctccccgacc accaagttcc acgtcctgac cgcccagctg tctttccctc gctctgcccg     60
taattctgat ctccaggccg gattccaagt gctgtcgtct gacctcgaaa gcaccactat    120
ctactaccag ttctccaatg agtcaatcat cgtcgaccgc agcaacacca gtgctgccgc    180
gaagaccacc aatggaatcg tcagcaccaa tgagtctgga cgtctccggt tgttcgattt    240
gcagggcgat gcccaggaaa ttgagactct ggacctcacg gtcgttgtgg ataactctgt    300
cctcgagatc tatgccaatg gacgttttgc cctgagtact tgggctcggt atgtattctg    360
tgatggtcga caacaaggca ttggctaaca atctttcgca gttcctggta caagaactcg    420
actgacatca agttcttcca caacggtgcg ggtgaagtga cattcagcaa tgttactgtc    480
tccgagggcc tgtttgaagc ctggcctgag cgtgtctaat gtaagatatt gtgatggggt    540
agggaaaggg ttgcttgtat atatgagctc gatgtcatgg aaagtaaaat ctgtggtcga    600
gttaataatt ataaaaccta gttagttcag agtaatccat ctggttgtac atttcgtgaa    660
ttcttcaaaa cggcatacca ccgctggacc tctgggctgg cgatcgactc gggaagccga    720
gaacaggcga gcccggcaaa ccacctcgcc ggccgccgga gaccaggtta tcgatgtgaa    780
agtgtgccca aacgtcactt ccaaagtcta ttaaagaata cttcgtatcc atgaccaggt    840
ttgatacctg aagggaaact ccctggaaat aaactcatga tcacctcgtt cacctaatca    900
atatggttaa gccgagccgt ccctccacaa gcgtcatctt ccacgacggt gactatgacg    960
cgcacatgaa ctacgataaa aatcgctcat agatataacg attacccat aaccggacgg   1020 gccgatcatt gcgtttattt tgtccctgtc ctgttgcctg aacgccggcg gaactgtatg   1080
ttgaccggaa ccgatcatcg aaaggtcagg ttccggcgga accgaacaca ctcaacccca   1140
tgggcagact actccaggtt tcgactccgg attatgacta tcattctaga ctagtgtcta   1200
gtgataatcc actcaatggt tcgcaattgt ggggctacag tgactatgta gtcttgggtt   1260
acagtttgtt ggagagtggg gatgtatatc ctggggtatt gtagattagt ataaaaccac   1320
acacggatcc ccacgtgtat ggtaggtatc cctaagtgtg ctcatattgt tcacttgtgt   1380
catactatta gtgcaccgaa                                              1400

<210> SEQ ID NO 43
<211> LENGTH: 611
<212> TYPE: DNA
<213> ORGANISM: Aspergillus oryzae
<220> FEATURE:
<221> NAME/KEY: promoter
<222> LOCATION: (1)..(611)
<223> OTHER INFORMATION: Aspergillus oryzae sorB promoter, PsorB.

<400> SEQUENCE: 43
```

```
gacgcagtgt ccctgtatta aaagctgtac gataaaacgt ataatagaat ggaatgactt      60
gacatcatga tttggtggta ctttcgttgc gcctctggaa tctacgcgaa aatgaatgaa     120
attgacgagt actaaactgt ccaacactga tgttgacaaa caacatcgag caagatcggc     180
tcacttattc aataaggagg tagggtttca tatcgcgctg ttagcgctgt caaggcgagt     240
agtcgccaat ccgagtctct gggcgaaggc tttgctttgc ttcatcgggc cggaagggtc     300
cgtttctatg cgcagtgaaa ctgtgaaaga ccattaggca tacaccaacc gagtaaagga     360
tcagcgggag aaattaaagt cagatagaac agctcataag ttctccattt cccccacgac     420
cccgcaggtc ccaagctgga gatgtgagac cggaaccgaa gtgtggttgt tccgccggaa     480
ccgtgatgcc gatgaacata ctacttattt caataggccc ttcagcgatt ataaggatgc     540
agtttaaatc ttccttttt catttctcca gattcacccc tgaataccttt gtttagagtt     600 tagggagcaa a                                                         611
```

<210> SEQ ID NO 44
<211> LENGTH: 28
<212> TYPE: DNA
<213> ORGANISM: artificial sequence
<220> FEATURE:
<223> OTHER INFORMATION: Primer HTJP-2

<400> SEQUENCE: 44
ccgcacgtgt caagcaaccc caatccgc                                        28

<210> SEQ ID NO 45
<211> LENGTH: 37
<212> TYPE: DNA
<213> ORGANISM: artificial sequence
<220> FEATURE:
<223> OTHER INFORMATION: Primer HTJP-3

<400> SEQUENCE: 45
cgcggatcca ccatgggtgt caatttcaaa gttcttg                              37

<210> SEQ ID NO 46
<211> LENGTH: 21
<212> TYPE: DNA
<213> ORGANISM: artificial sequence
<220> FEATURE:
<223> OTHER INFORMATION: Primer HTJP-24

<400> SEQUENCE: 46
ccgcaacaac aggttacaaa g                                               21

<210> SEQ ID NO 47
<211> LENGTH: 20
<212> TYPE: DNA
<213> ORGANISM: artificial sequence
<220> FEATURE:
<223> OTHER INFORMATION: Primer HTJP-25

<400> SEQUENCE: 47
ccaggttacc catttcgatg                                                 20

<210> SEQ ID NO 48
<211> LENGTH: 44
<212> TYPE: DNA
<213> ORGANISM: artificial sequence
<220> FEATURE:
<223> OTHER INFORMATION: Primer HTJP-231

<400> SEQUENCE: 48
ctaactacta actaggttaa ttaactcccc gaccaccaag ttcc                     44

<210> SEQ ID NO 49
<211> LENGTH: 36
<212> TYPE: DNA
<213> ORGANISM: artificial sequence
<220> FEATURE:
<223> OTHER INFORMATION: Primer HTJP-232

<400> SEQUENCE: 49
aaaatacttt actagtgcat gcatgaggtc tttttg                              36

<210> SEQ ID NO 50
<211> LENGTH: 41
<212> TYPE: DNA
<213> ORGANISM: artificial sequence
<220> FEATURE:
<223> OTHER INFORMATION: Primer HTJP-233

<400> SEQUENCE: 50
gcccttcatg gtggctagct tcggtgcact aatagtatga c                        41

<210> SEQ ID NO 51
<211> LENGTH: 39
<212> TYPE: DNA
<213> ORGANISM: artificial sequence
<220> FEATURE:
<223> OTHER INFORMATION: Primer HTJP-234

<400> SEQUENCE: 51
gtgcaccgaa gctagccacc atgaagggca tcctcggcc                           39

<210> SEQ ID NO 52
<211> LENGTH: 30
<212> TYPE: DNA
<213> ORGANISM: artificial sequence
<220> FEATURE:
<223> OTHER INFORMATION: Primer HTJP-235

<400> SEQUENCE: 52
ccttaattaa gacgcagtgt ccctgtatta                                     30

<210> SEQ ID NO 53
<211> LENGTH: 30
<212> TYPE: DNA
<213> ORGANISM: artificial sequence
<220> FEATURE:
<223> OTHER INFORMATION: Primer HTJP-236

<400> SEQUENCE: 53
ctagctagct ttgctcccta aactctaaac                                     30

<210> SEQ ID NO 54
<211> LENGTH: 35
<212> TYPE: DNA
<213> ORGANISM: artificial sequence
<220> FEATURE:
<223> OTHER INFORMATION: Primer HTJP-280

<400> SEQUENCE: 54
agttaattaa gctagcctcc ccgaccacca agttc                               35

<210> SEQ ID NO 55
<211> LENGTH: 36

```
<212> TYPE: DNA
<213> ORGANISM: artificial sequence
<220> FEATURE:
<223> OTHER INFORMATION: Primer HTJP-281

<400> SEQUENCE: 55
gtaagactga gctagcgcat gcatgaggtc tttttg                    36

<210> SEQ ID NO 56
<211> LENGTH: 31
<212> TYPE: DNA
<213> ORGANISM: artificial sequence
<220> FEATURE:
<223> OTHER INFORMATION: Primer HTJP-282

<400> SEQUENCE: 56
agttaattaa gctagcgacg cagtgtccct g                         31

<210> SEQ ID NO 57
<211> LENGTH: 29
<212> TYPE: DNA
<213> ORGANISM: artificial sequence
<220> FEATURE:
<223> OTHER INFORMATION: Primer HTJP-341

<400> SEQUENCE: 57
ccttaattaa ggatgtggac gggttatcg                            29

<210> SEQ ID NO 58
<211> LENGTH: 26
<212> TYPE: DNA
<213> ORGANISM: artificial sequence
<220> FEATURE:
<223> OTHER INFORMATION: Primer HTJP-342

<400> SEQUENCE: 58
ctagctagcg ttaccggcag ggaagg                               26
```

REGULATED PEPC EXPRESSION

CROSS-REFERENCE TO RELATED APPLICATION

This application is a 35 U.S.C. § 371 national application of PCT/EP2014/067949 filed Aug. 22, 2014, which claims priority or the benefit under 35 U.S.C. § 119 of European application no. 13181603.5 filed Aug. 23, 2013, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a recombinant fungal host cell comprising at least one first polynucleotide encoding a polypeptide of interest; and one or more second polynucleotide encoding a fungal PepC protease, wherein the one or more second polynucleotide is operably linked to a regulated heterologous promoter, as well as a method for producing a polypeptide of interest, comprising cultivating said fungal host cell.

BACKGROUND OF THE INVENTION

Finding new ways to improve yield and/or storage stability is of continued interest in the area of industrial polypeptide manufacture. It has been shown in both fungal and bacterial recombinant host cells that inactivation of one or more proteolytic enzyme, often by deleting the encoding gene(s), can lead to improved yield and/or storage stability.

However, there are also examples where the inactivation of a proteolytic enzyme in a host cell has had undesirable consequences for the host cell phenotype. One such example is the inactivation of the PepC protease in an *Aspergillus fumigutus* host, wherein the PepC inactivation was shown to reduce sporulation and growth rate significantly, as reported by Reichard U. et al. (2000, Int J Med Microbiol. 290, 549-558).

In the biotech industry it is very important that a fungal recombinant production host cell retains its ability to sporulate, in order to be able to make cell-bank preparations, a crucial requirement for consistent polypeptide manufacture.

SUMMARY OF THE INVENTION

The inventors of the instant application have demonstrated that the inactivation of the PepC protease in *Aspergillus oryzae* or *A. niger* results in a much improved yield and/or stability of at least 3 different polypeptides, a lipase, a cutinase and an asparaginase. Unfortunately, the inactivation of the PepC protease also severely impeded the sporulation ability of the cells (see Examples below), not entirely unexpected in view of Reichard U. et al (vide supra).

Despite this negative result, the inventors went ahead and they succeeded in operably linking a PepC-encoding polynucleotide to one of several different regulated promoters, which were repressed or non-induced during typical cultivation conditions suitable for the industrial manufacture of polypeptides, but which could be induced or de-repressed by the presence of specific compounds leading to expression of PepC and, thus, to a normal sporulation phenotype.

In other words, the inventors have successfully constructed a highly desirable fungal host cell for the industrial manufacture of polypeptides, which has a toggle-switch controlling high yield (PepC inactivation) versus sporulation (PepC expression), depending on the conditions. As shown in the Examples below, these fungal host cells showed up to five times higher production yield than the wild-type, while the their number of spores produced in slant tubes was about one order of magnitude higher than the ΔPepC strain.

Accordingly, in a first aspect the invention relates to a recombinant fungal host cell comprising:
  a) at least one first polynucleotide encoding a polypeptide of interest; and
  b) one or more second polynucleotide encoding a fungal PepC protease, wherein the one or more second polynucleotide is operably linked to a regulated heterologous promoter.

In a second aspect the invention relates to a method of producing a polypeptide of interest, said method comprising the steps of:
  a) cultivating a host cell as defined in any of the preceding claims, under conditions suitable for the production of the polypeptide of interest; and, optionally
  b) recovering the polypeptide of interest.

Figure 5:
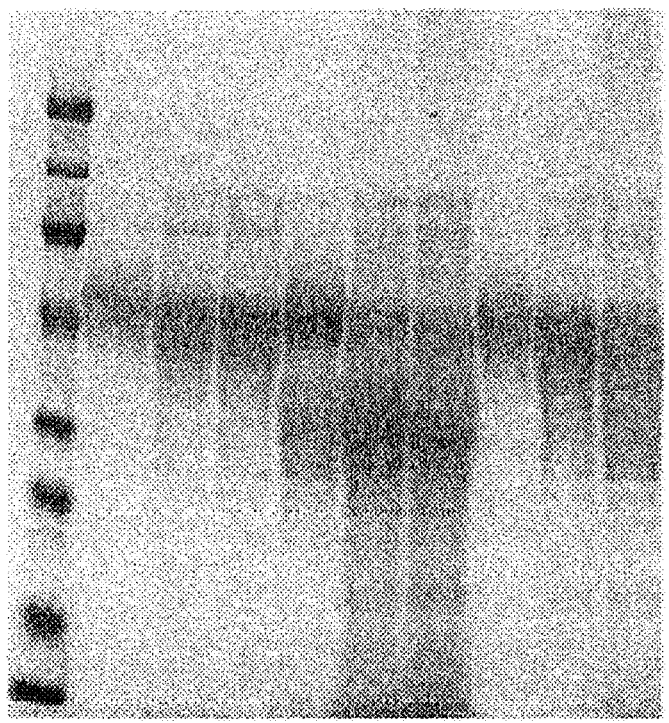

FIG. 5 shows a photo of a Coomassie blue stained SDS-PAGE gel, where fermentation samples from the *A. niger* strains in Examples 7 were analysed to see and compare the degree of degradation of the asparaginase product. As expected, the samples from strain 50-4C-9 (native PepC expression) were severely degraded in the presence of PepC (FIG. 5, lanes 5-7), whereas the asparaginase expressed in strain 50-C2948-9 (ΔPepC) was considerably more stable (FIG. 5, lanes 8-10). The degradation in the samples from strain 107-C2948-20 (niaD-promoter PepC expression) also showed significantly less degradation of asparaginase (FIG. 5, lanes 2-4, suggesting that PepC expression by the niaD promoter was strongly repressed under the tank fermentation conditions.

DEFINITIONS cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequence that provide for its expression.

Fragment: The term "fragment" means a polypeptide having one or more (e.g., several) amino acids absent from the amino and/or carboxyl terminus of a mature polypeptide; wherein the fragment has retained its activity, e.g., an enzyme fragment is a fragment of an enzyme that retains its enzymatic activity.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent Identity and is calculated as follows:

(Identical Deoxyribonucleotides×100)/(Length of
Alignment−Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment retaining its activity.

Variant: The term "variant" means a polypeptide, e.g., an enzyme, comprising an alteration, a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

Host Cells

The present invention relates to recombinant fungal host cells, comprising at least one first polynucleotide encoding a polypeptide of interest operably linked to one or more control sequences that direct the production of a polypeptide, and comprising one or more second polynucleotide encoding a fungal PepC protease, wherein the one or more second polynucleotide is operably linked to a regulated heterologous promoter.

A DNA construct or expression vector comprising the at least first and/or the one or more second polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a filamentous fungal cell. "Filamentous fungi" include all filamentous forms of the subdivision Eumycota and Oomycota (as defined by Hawksworth at al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium*

*queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787.

A preferred embodiment of the invention relates to the host cell of the first aspect, wherein the at least one first polynucleotide is present in chromosome of the host cell; preferably the at least one first polynucleotide is present in chromosome of the host cell in two or more copies.

In a preferred embodiment the polypeptide of interest is an enzyme selected from the group consisting of a hydrolase, an isomerase, a ligase, a lyase, an oxidoreductase and a transferase; preferably the polypeptide of interest is an enzyme selected from the group consisting of an alpha-galactosidase, alpha-glucosidase, aminopeptidase, amylase, asparaginase beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase or xylanase.

PepC Protease

In a preferred embodiment, the PepC protease is selected from the group consisting of:

a) a polypeptide comprising an amino acid sequence at least 80% identical to the mature sequence shown in positions 1 to 380 of SEQ ID NO:2 or in position 1 to 418 of SEQ ID NO: 4; preferably at least 85%, at least 90%, at least 91%, at least 92%, at least 93%, at least 94%, at least 95%, at least 96%, at least 97%, at least 98%, at least 99%, or 100% identical to the mature sequence shown in positions 1 to 380 of SEQ ID NO:2 or in position 1 to 418 of SEQ ID NO: 4;

b) a polypeptide encoded by a polynucleotide that hybridizes under medium stringency conditions with (i) the mature polypeptide coding sequence of SEQ ID NO: 1 or SEQ ID NO:2; preferably under medium-high stringency conditions, high stringency conditions, or very high stringency conditions (as defined herein), or (ii) the full-length complement of (i);

c) a polypeptide encoded by a polynucleotide comprising a nucleotide sequence at least 80% identical to the mature polypeptide coding sequence of SEQ ID NO: 1 or SEQ ID NO: 3; preferably at least 85%, at least 90%, at least 91%, at least 92%, at least 93%, at least 94%, at least 95%, at least 96%, at least 97%, at least 98%, at least 99%, or 100% identical to the mature polypeptide coding sequence of SEQ ID NO: 1 or SEQ ID NO: 3;

d) a variant of the mature polypeptide of SEQ ID NO: 2 or SEQ ID NO: 4 comprising a substitution, deletion, and/or insertion at one or more positions; and e) a fragment of the polypeptide of (a), (b), (c), or (d) that has protease activity.

A PepC protease of the present invention preferably comprises or consists of the amino acid sequence of SEQ ID NO: 2 or SEQ ID NO:4 or an allelic variant thereof; or is a fragment thereof having protease activity. In another aspect, the polypeptide comprises or consists of the mature polypeptide of SEQ ID NO: 2 or SEQ ID NO: 4. In another aspect, the polypeptide comprises or consists of amino acids 1 to 380 of SEQ ID NO: 2 or amino acids 1 to 418 of SEQ ID NO: 4.

In another embodiment, the present invention relates to an isolated PepC protease encoded by a polynucleotide that hybridizes under medium stringency conditions, medium-high stringency conditions, high stringency conditions, or very high stringency conditions with (i) the mature polypeptide coding sequence of SEQ ID NO: 1 or SEQ ID NO: 3, or (ii) the full-length complement of (i) (Sambrook et al., 1989, *Molecular Cloning, A Laboratory Manual*, 2d edition, Cold Spring Harbor, N.Y.)

The polynucleotide of SEQ ID NO: 1 or SEQ ID NO: 3 or a subsequence thereof, as well as the polypeptide of SEQ ID NO: 2 or SEQ ID NO: 4, or a fragment thereof, may be used to design nucleic acid probes to identify and clone DNA encoding PepC protease polypeptides from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a PepC protease polypeptide. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or SEQ ID NO: 3, or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 3; (ii) the mature polypeptide coding sequence of SEQ ID NO: 1 or SEQ ID NO: 3; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is nucleotides 1 to 1485, nucleotides 49 to 1485, or nucleotides 346 to 1485 of SEQ ID NO: 2. In another aspect, the nucleic acid probe is nucleotides 1 to 1599, nucleotides 49 to 1599, or nucleotides 346 to 1599 of SEQ ID NO: 3. In yet another aspect, the nucleic acid probe is a polynucleotide that encodes the polypeptide of SEQ ID NO: 2 or SEQ ID NO: 4; the mature polypeptide thereof; or a fragment thereof. In another aspect, the nucleic acid probe is SEQ ID NO: 1 or SEQ ID NO: 3.

In another embodiment, the present invention relates to a PepC polypeptide encoded by a polynucleotide having a sequence identity to the mature polypeptide coding sequence of SEQ ID NO: 1 or SEQ ID NO: 3 of at least 80%, at least 85%, at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptide of SEQ ID NO: 2 or SEQ ID NO: 4 comprising a substitution, deletion, and/or insertion at one or more (e.g., several) positions. In an embodiment, the number of amino acid substitutions, deletions and/or insertions introduced into the mature polypeptide of SEQ ID NO: 2 or SEQ ID NO: 4 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/lie, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, J. Biol. Chem. 271: 4699-4708.

The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

A PepC protease polypeptide of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The PepC protease polypeptide may be a fungal polypeptide. For example, the PepC polypeptide may be a yeast polypeptide such as a *Candida, Kluyveromyces, Pichia, Saccharomyces, Schizosaccharomyces*, or *Yarrowia* polypeptide; or a filamentous fungal polypeptide such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosparia, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide.

In another aspect, the PepC protease polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide.

In another aspect, the PepC polypeptide is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the Identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to PepC-encoding polynucleotides, as described herein.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application, Academic Press*, New York. Other nucleic acid amplification procedures such as ligase chain reaction (LCR), ligation activated transcription (LAT) and polynucleotide-based amplification (NASBA) may be used. The polynucleotides may be cloned from a strain of *Aspergillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 or SEQ ID NO: 3, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the at least first polynucleotide of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

Examples of suitable promoters for directing transcription of the one or more second polynucleotide encoding a fungal PepC protease of the present invention in a filamentous fungal host cell are regulated heterologous promoters; preferably the regulated heterologous promoter is induced or repressed in the presence of a specific compound; more preferably the regulated heterologous promoter is induced in the presence of nitrate and repressed in the presence of ammonium; preferably the regulated heterologous promoter is a filamentous fungal nitratereductase promoter; more preferably the regulated heterologous promoter is a nitratereductase promoter from an *Aspergillus* or a *Trichoderma* cell; even more preferably the regulated heterologous promoter is a nitratereductase promoter from *Aspergillus niger, Aspergillus oryzae* or *Trichoderma reesei*; most preferably the regulated heterologous promoter is the niaD nitratereductase promoter from *Aspergillus niger, Aspergillus oryzae* or *Trichoderma reesei*; most preferably the regulated heterologous promoter comprises a nucleotide sequence at least 80% identical to SEQ ID NO: 41; preferably at least 85%, at least 90%, at least 95%, at least 96%, at least 97%, at least 98%, at least 99%, or 100% % identical to SEQ ID NO: 41.

In another preferred embodiment, the regulated heterologous promoter is induced in the presence of sorbitol and repressed in the absence of sorbitol; preferably the regulated heterologous promoter is a filamentous fungal sorbitol transporter promoter or a sorbitol dehydrogenase promoter from an *Aspergillus* or *Trichoderma* cell; even more preferably the regulated heterologous promoter is a sorbitol transporter promoter or a sorbitol dehydrogenase promoter from *Aspergillus niger, Aspergillus oryzae* or *Trichoderma reesei*; most preferably the regulated heterologous promoter is the sorA or sorB promoter from *Aspergillus niger, Aspergillus oryzae* or *Trichoderma reesei*; most preferably the regulated heterologous promoter comprises a nucleotide sequence at least 80% identical to SEQ ID NO: 42 or SEQ ID NO: 43; preferably at least 85%, at least 90%, at least 95%, at least 96%, at least 97%, at least 98%, at least 99%, or 100% identical to SEQ ID NO. 42 or SEQ ID NO. 43.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be an mRNA stabilizer region downstream of a promoter and upstream of the coding sequence of a gene which increases expression of the gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola Insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphorihosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

In a preferred embodiment of the present, the PepC protease is expressed with a pro-peptide selected from the group consisting of:
 a) a pro-peptide comprising an amino acid sequence at least 80% identical to that shown in positions −99 to −1 of SEQ ID NO: 2 or in positions −99 to −1 of SEQ ID NO: 4; preferably at least 85%, at least 90%, at least 91%, at least 92%, at least 93%, at least 94%, at least 95%, at least 96%, at least 97%, at least 98%, at least 99%, or 100% identical to the mature sequence shown in positions −99 to −1 of SEQ ID NO:2 or in position −99 to −1 of SEQ ID NO: 4;
 b) a pro-peptide encoded by a polynucleotide that hybridizes under medium stringency conditions with (i) the pro-peptide coding sequence of SEQ ID NO: 1 or SEQ ID NO:2, preferably under medium-high stringency conditions, high stringency conditions, or very high stringency conditions (as defined herein), or (ii) the full-length complement of (i); or
 c) a pro-peptide encoded by a polynucleotide having a nucleotide sequence at least 80% identical to the pro-peptide coding sequence of SEQ ID NO: 1 or SEQ ID NO: 3, preferably at least 85%, at least 90%, at least 91%, at least 92%, at least 93%, at least 94%, at least 95%, at least 96%, at least 97%, at least 98%, at least 99%, or 100% identical to the pro-peptide coding sequence of SEQ ID NO: 1 or SEQ ID NO: 3.

In another preferred embodiment of the present invention, the PepC protease is expressed with a signal-peptide selected from the group consisting of:
 a) a signal-peptide comprising an amino acid sequence at least 80% identical to that shown in positions −115 to −100 of SEQ ID NO: 2 or in positions −115 to −100 of SEQ ID NO: 4 preferably at least 85%, at least 90%, at least 91%, at least 92%, at least 93%, at least 94%, at least 95%, at least 96%, at least 97%, at least 98%, at least 99%, or 100% identical to that shown in positions −115 to −100 of SEQ ID NO:2 or in position −115 to −100 of SEQ ID NO: 4;
 b) a signal-peptide encoded by a polynucleotide that hybridizes under medium stringency conditions with (i) the signal-peptide coding sequence of SEQ ID NO: 1 or SEQ ID NO:2; preferably under medium-high stringency conditions, high stringency conditions, or very high stringency conditions (as defined herein), or (ii) the full-length complement of (i); or
 c) a signal-peptide encoded by a polynucleotide having at least 80% sequence identity to the signal-peptide coding sequence of SEQ ID NO: 1 or SEQ ID NO: 3, preferably at least 85%, at least 90%, at least 91%, at least 92%, at least 93%, at least 94%, at least 95%, at least 96%, at least 97%, at least 98%, at least 99%, or 100% identical to the signal-peptide coding sequence of SEQ ID NO: 1 or SEQ ID NO: 3.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

EXAMPLES

Materials and Methods

General methods of PCR, cloning, ligation nucleotides etc. are well-known to a person skilled in the art and may for example be found in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

Media and Reagents

Chemicals used for buffers and substrates were commercial products of analytical grade:
- Cove: 342.3 g/L Sucrose, 20 ml/L COVE salt solution, 10 mM Acetamide, 30 g/L noble agar.
- Cove top agar: 342.3 g/L Sucrose, 20 ml/L COVE salt solution, 10 mM Acetamide, 10 g/L low melt agarose
- Cove-2: 30 g/L Sucrose, 20 ml/L COVE salt solution, 10 mM Acetamide, 30 g/L noble agar.
- COVE salt solution is composed of 26 g KCl, 26 g $MgSO_4.7H_2O$, 76 g $KH_2PO_4$ and 50 ml Cove trace metals, water to 1 litre.
- Trace metal solution for COVE is composed of 0.04 g $NaB_4O_7.10H_2O$, 0.4 g of $CuSO_4.5H_2O$, 1.2 g of $FeSO_4.7H_2O$, 1.0 g of $MnSO_4.H_2O$, 0.8 g of Neutral amylase II $MoO2.2H_2O$, and 10.0 g of $ZnSO_4.7H_2O$, water to 1 litre.
- Cove-N top agarose is composed of 342.3 g of Sucrose, 20 ml of COVE salt solution, 3 g of $NaNO_3$, and 10 g of low melt agarose, water to 1 litre.
- Amyloglycosidase trace metal solution is composed of 6.8 g $ZnCl_2.7H_2O$, 2.5 g $CuSO_4.5H_2O$, 0.24 g $NiCl_2.6H_2O$, 13.9 g $FeSO_4.7H_2O$, 13.5 g $MnSO_4$—$H_2O$ and 3 g citric acid, water to 1 litre.
- YPG is composed of 4 g of yeast extract, 1 g of $KH_2PO_4$, 0.5 g of $MgSO_4.7H_2O$ and 15 g of Glucose (pH 6.0), water to 1 litre.
- STC buffer is composed of 0.8 M of sorbitol, 25 mM of Tris (pH 8), and 25 mM of $CaO_2$, water to 1 litre.
- STPC buffer is composed of 40% PEG4000 in STC buffer.
- MSS is composed of 70 g Sucrose, 100 g Soybean powder (pH 6.0), water to 1 litre.
- MU-1 is composed 260 g of Maltodextrin, 3 g of $MgSO_4.7H_2O$, 5 g of $KH_2PO_4$, 6 g of $K_2SO_4$, amyloglycosidase trace metal solution 0.5 ml and urea 2 g (pH 4.5), water to 1 litre.
- MU-1 glu is composed 260 g of glucose, 3 g of $MgSO_4.7H_2O$, 5 g of $KH_2PO_4$, 6 g of $K_2SO_4$, amyloglycosidase trace metal solution 0.5 ml and urea 2 g (pH 4.5), water to 1 litre.

PCR Amplifications in Examples 1-4.

All PCR amplifications was performed in a volume of 100 microL containing 2.5 units Taq polymerase, 100 ng of pSO2, 250 nM of each dNTP, and 10 pmol of each of the two primers described above in a reaction buffer of 50 mM KCl, 10 mM Tris-HCl pH 8.0, 1.5 mM MgCl2. Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C.

PCR Amplifications in Examples 5-8:

| Component | Volume | Final Concentration |
|---|---|---|
| 10x Buffer for KOD -Plus- | 5 µl | 1x |
| 2 mM dNTPs | 5 µl | 0.2 mM each |
| 25 mM $MgSO_4$ | 2 µl | 1.0 mM |
| 10 pmol/µl Primer #1 | 1.5 µl | 0.3 µM |
| 10 pmol/µl Primer #2 | 1.5 µl | 0.3 µM |
| Template DNA | X µl | |
| Genomic DNA | 10-200 ng/50 µl | |
| Plasmid DNA | 1-50 ng/50 µl | |
| PCR grade water | Y µl | |
| KOD-Plus- (1.0 U/µl) | 1 µl | 1.0 U/50 µl |
| Total reaction volume | 50 µl | |

3-step Cycle:

Pre-denaturation: 94° C., 2 min.
Denaturation: 94° C., 15 sec. ⎤
Annealing: Tm-[5-10]° C.*, 30 sec. ⎥ 35 cycles
Extension: 68° C., 1 min./kb ⎦

*Aspergillus oryzae* Transformation

*Aspergillus* transformation was done as described by Christensen et al.; Biotechnology 1988 6 1419-1422. In short, *A. oryzae* mycelia were grown in a rich nutrient broth. The mycelia were separated from the broth by filtration. The enzyme preparation Glucanex® (Novozymes) was added to the mycelia in osmotically stabilizing buffer such as 1.2 M $MgSO_4$ buffered to pH 5.0 with sodium phosphate. The suspension was incubated for 60 minutes at 37 degrees ° C. with agitation. The protoplast was filtered through miracloth to remove mycelial debris. The protoplast was harvested and washed twice with STC (1.2 M sorbitol, 10 mM $CaCl_2$, 10 mM Tris-HCl pH 7.5). The protoplasts were finally re-suspended in 200-1000 microl STC.

For transformation, 5 microgram DNA was added to 100 microl protoplast suspension and then 200 microl PEG solution (60% PEG 4000, 10 mM $CaCl_2$, 10 mM Tris-HCl pH 7.5) was added and the mixture is incubated for 20 minutes at room temperature. The protoplast were harvested and washed twice with 1.2 M sorbitol. The protoplast was finally re-suspended 200 microl 1.2 M sorbitol. Transformants containing the amdS gene were selected for its ability to used acetamide as the sole source for nitrogen on minimal plates (Cove D. J. 1966. Biochem. Biophys. Acta. 113:51-56) containing 1.0 M sucrose as carbon source, 10 mM acetamide as nitrogen source. After 5-7 days of growth at 37 degrees ° C., stable transformants appeared as vigorously growing and sporulating colonies. Transformants were purified twice through conidiospores.

*Aspergillus niger* Transformation

*Aspergillus* transformation was done as described by Christensen et al.; Biotechnology 1988 6 1419-1422. The preferred procedure is described below.

The *Aspergillus niger* host strain was inoculated to 100 ml of YPG medium supplemented with 10 mM uridine and incubated for 16 hrs at 32° C. at 80 rpm. Pellets were collected and washed with 0.6 M KCl, and resuspended 20 ml 0.6 M KCl containing a commercial β-glucanase product (GLUCANEX™, Novozymes A/S, Bagsværd, Denmark) at a final concentration of 20 mg per ml. The suspension was incubated at 32° C. at 80 rpm until protoplasts were formed, and then washed twice with STC buffer. The protoplasts were counted with a hematometer and resuspended and adjusted in an 8:2:0.1 solution of STC:STPC:DMSO to a final concentration of $2.0 \times 10^7$ protoplasts/ml. Approximately 4 μg of plasmid DNA was added to 100 μl of the protoplast suspension, mixed gently, and incubated on ice for 30 minutes. One ml of SPTC was added and the protoplast suspension was incubated for 20 minutes at 37° C. After the addition of 10 ml of 50° C. Cove or Cove-N top agarose, the reaction was poured onto Cove agar plates and the plates were incubated at 32° C. for 5 days.

Shake Flask Fermentation

Shake flask containing 10 ml YPM medium (2 g/l yeast extract, 2 g/l peptone, and 2% maltose) were inoculated with spores from a transformant strain and incubated at 30 degrees ° C., 200 rpm for 4 days.

*Aspergillus oryzae* Fermentation Protocol

Seed cultivation: Spores from solid minimal medium (Cove (1966) Biochimica et *Biophysica Acta,* 113. 51-56) slant were transferred to shake flask (glycerol 20 g/L, yeast extract 18 g/L) and incubated for 1 day at 30° C. and 250 rpm.

Fed Batch Fermentation:

Tank medium (sucrose 24 g/L, yeast extract 10 g/L, $(NH_4)_2SO_4$ 5 g/L, $MgSO_4 \cdot 7H_2O$ 2 g/L, $K_2SO_4$ 2 g/L, citric acid 1 g/L, $KH_2PO_4$ 2 g/L trace metal solution 0.5 ml/L) was adjusted to 34° C. Aeration was 1 vvm and pH was controlled at 6.0 using 10% $NH_4OH$. Main medium was inoculated from seed cultivation. When pH>6.4 feeding (400 g/L maltose syrup, 1 g/L citric acid) was started at a rate of 3.33 g/L/h. Stirrer speed was controlled to avoid too low (<20%) oxygen tension.

Lab-scale Tank Cultivation for Asparaginase Production

Fermentation was done as fed-batch fermentation (H. Pedersen 2000, Appl Microbiol Biotechnol, 53: 272-277). Selected strains were pre-cultured in liquid media then grown mycelia were transferred to the tanks for further cultivation of enzyme production. Cultivation was done at pH 4.75 at 34° C. for 7 days with the feeding of glucose and ammonium without over-dosing which prevents enzyme production. Culture supernatant after centrifugation was used for enzyme assay.

SDS-page

Lipase/cutinase: SDS gel used was Criterion™ XT precast gels, 10% Bis-Tris, from BioRad and was run and stained with coomassie blue as recommend by the manufacturer.

Asparaginase: The culture supernatants were subjected to SDS-PAGE analysis. SDS-PAGE was performed by using e.Pagel 12.5% E-R12.5L (#2331720, ATTO) with miniPAGE (pageRun) system (# AE-6531, ATTO). Twenty ul of samples was loaded on the gel (Ten μl of each sample was mixed with 10 ul of loading buffer). Ten ul of MW Marker: (Prestained SDS-PAGE standard, BioRad #161-0318) was also applied. The gel was electrophoresed at a constant current of 20 mA for 80 min in 1×SDS buffer (BioRad). The protein bands were stained by CBB Stain One (Nakarai).

Genes pyrG: This gene codes for orotidine-5'-phosphate decarboxylase, an enzyme involved in the biosynthesis of uridine.

amdS: This gene codes for acetamidase, an enzyme involved in metabolism of acetamide.

Plasmids pCOIs1124 is described in patent appl. PCT/EP2013/061052, filed 29 May 2013.
pCOIs1126 is described in patent appl. PCT/EP2013/061052, filed 29 May 2013.
pCOIs1130 is described in patent appl. PCT/EP2013/061052, filed 29 May 2013.
pCOIs1148 is described in patent appl. PCT/EP2013/061052, filed 29 May 2013.
pCOIs1150 is described in example 2
pCOIs1151 is described in example 2
pCOIs1152 is described in example 2
pCOIs1175 is deserted in example 2
pCOIs1197 is described in example 2
pCOIs1198 is described in example 2
pCOIs1202 is described in example 2
pCOIs1360 is described in example 2
pCOIs1386 is described in example 2
pCOIs1387 is described in example 2
pCR-4 Blunt-TOPO is from Invitrogen.
pDAu689 is described in example 4
pHUda797 is described in patent US2013095525, example 1
pJaL554 is described in patent WO07045248, example 9
pJaL617 is described in example 1
pJaL619 is described in example 1
pJaL620 is described in example 1
pMLxN31 is described in example 3
pMT1335 is described in patent WO 98/12300, example 2
pMT3536 is described in example 1
The TOPO plasmid cloning kit (Invitrogen) and pBluescript II SK- (Stratagene #212206) were used for cloning of PCR fragments.
pIN001 is described in WO2008110513.
pHUda801 harbouring *A. nidulans* pyrG gene and herpes simplex virus (HSV) thymidine kinase gene (TK) driven by *A. nidulans* glyceraldehyde-3-phosphate dehydrogenase promoter (Pgpd) and *A. nidulans* tryptophane synthase terminator (TtrpC) is described in example 4 in WO2012/160093.
pRika147 enzyme expression vector is described in WO2012/160093, example 9. pHUda1306 is described in WO2012/160093, Example 14

Strains

*Escherichia coli* DH5-alpha (Toyobo) is used for plasmid construction and amplification.
*Aspergillus oryzae* NBRC4177: available from Institute for fermentation, Osaka; 17-25 Juso Hammachi 2-Chome Yodogawa-Ku, Osaka, Japan.
*Aspergillus oryzae* COIs454 is described in patent WO2012160093, example 16
*Aspergillus oryzae* DAu712 is described in example 4
*Aspergillus oryzae* DAu729 is described in example 4
*Aspergillus oryzae* MLxN56 is described in example 1
*Aspergillus oryzae* MLxN69 is described in example 3
*Aspergillus oryzae* MLxN70 is described in example 3
*Aspergillus oryzae* RUNG237 is described in example 1
*Aspergillus oryzae* RIB40/ATCC 42149 was used as a gene source for promoter sequences; its parent host (NN059280) is described in WO 2012/160093, example 13.
*Aspergillus niger* strain C2948 is a pepC gene deficient derivative of NN059280. The pyrG gene rescue of C2948 was performed to generate C2948-6 as described in WO 2012/160093.

Sequences

SEQ ID NO: 1:
*Aspergillus oryzae* PepC coding DNA sequence

SEQ ID NO: 2:
*Aspergillus oryzae* PepC protease

SEQ ID NO: 3:
*Aspergillus niger* PepC coding DNA sequence

-continued

SEQ ID NO: 4:
Aspergillus niger PepC protease

SEQ ID NO: 5: Primer oJaL113
5'-gagctgctggatttggct

SEQ ID NO: 6: Primer oJaL114
5'-ccaacagccgactcaggag

SEQ ID NO: 7: Primer oJaL228
5'-accagcagcaacggcgaag

SEQ ID NO: 8: Primer oJaL229
5'-ggccttccctgccggtaacatgagaggcatcctcggcc

SEQ ID NO: 9: Primer oJaL230
5'-ggccgaggatgcctctcatgttaccggcagggaaggcc

SEQ ID NO: 10: Primer oJaL231
5'-cgtccacgcggggattatgcggatgtggacgggttatcgg

SEQ ID NO: 11: Primer oJaL232
5'-ccgataacccgtccacatccgcataatccccgcgtggacg

SEQ ID NO: 12: Primer oJaL233
5'-taatcactccgaaaggtcccccccgtcaaggagcttatcg

SEQ ID NO: 13: Primer oJaL234
5'-cgataagctccttgacggggggaccttcggagtgatta

SEQ ID NO: 14: Primer oJaL235
5'-gcacagccgtagtgggag

SEQ ID NO: 15: Primer B2103F03
5'-actagttagaatgctggaccagccccg

SEQ ID NO: 16: Primer B2103F04
5'-aagcttatttgtctctgacacac

SEQ ID NO: 17: Primer P801
5'-gaaacctgtcgtgccagttaattaagagagagttgaacctggacgc

SEQ ID NO: 18: Primer P802
5'-gcggccgcttttttttgcgatcgcggtgactgacacctggcggtag

SEQ ID NO: 19: Primer P803
5'-gcgatcgcaaaaaaaagcggccgccccagttgtgtatatagagg

SEQ ID NO: 20: Primer P804
5'-gccgattcattaatgcagggcgcgcctgaatgtataagctagcttccg

SEQ ID NO: 21: Primer P805
5'-tagcttatacattcaggcgcgccttcggtaaatacactatcacacac

SEQ ID NO: 22: Primer P806
5'-gattcattaatgcagggcgcggtttaaacattagtgataccccact
ctaag SEQ ID NO: 23: Primer P830
5'-aaaaaaggccttcttggccccacacaacatacgagccgg SEQ ID NO: 24: Primer P831
5'-aaaaaagctttatacattcaaatatgtatccgctc SEQ ID NO: 25:
Humicola lanuginosa lipase variant coding sequence SEQ ID NO: 26: Primer P87b
5'-cagttgtcgcttggtgcatc SEQ ID NO: 27: Primer P882
5'-cttagagtggggtatcactaataagcttgtttctgcattaatgaatc
ggcc SEQ ID NO: 28: Primer P881
5'-aagcttattagtgataccccactctaag SEQ ID NO: 29: Primer P864
5'-aggacttcccctacggctccg SEQ ID NO: 30: Primer P200
5'-ccaactccgccgttgcatatc SEQ ID NO: 31: Primer P920
5'-ttttttttaattaattggcggtgatattgatggcac SEQ ID NO: 32: Primer P921
5'-aaaaaagcttgcatgcactagtttatacattcaaatatgtatc
cgctc SEQ ID NO: 33: Primer P922
5'-tagtgcatgccctagggtcgacttaagcaaggatttcttaac SEQ ID NO: 34: Primer P923
5'-cgaccctagggcatgcactagtctgtcagaccaagtttactcata
tatac SEQ ID NO: 35: Primer P924
5'-aaaaaagcttactagtgcatgcgtttctgcattaatgaatcggcc SEQ ID NO: 36: Primer MLxnoli20
5'-caactgggggcggccgcaccatgaagctactctctctgaccg SEQ ID NO: 37: Primer MLxnoli21
5'-gtcagtcaccgcgatcgctcaggggtgacgatg SEQ ID NO: 38:
Humicola insolens cutinase coding sequence SEQ ID NO: 39: Primer DAuP810
5'-caactgggggcggccgcaccatgaagttcttcaccacgatcctctcg SEQ ID NO: 40: Primer DAuP811
5'-gtcagtcaccgcgatcgtcacgccctaattcggtcgacgag SEQ ID NO: 41:
Aspergillus oryzae niaD promoter, PniaD.

SEQ ID NO: 42:
Aspergillus oryzae sorA promoter, PsorA.

SEQ ID NO: 43:
Aspergillus oryzae sorB promoter, PsorB.

Example 1

Construction of the A. oryzae PniaD-pepC Strain, MLxN56

Construction of amdS Deleted A. oryzae Strain, MT3625

For deletion of the A. oryzae amdS gene a plasmid denoted pMT3536 was constructed in the following way: By PCR with the primers B2103F03 and B2103F04 on A. oryzae genomic DNA a 2654 bp DNA fragment was amplified containing the entire amdS coding region, including 352 bp upstream sequences and 348 bp downstream sequences. At the same time restriction sites were added (a SpeI sites 5' to the amdS gene and a HindIII sites at the 3' to the amdS gene) at the end of the amplified DNA. The 2654 fragment was cloned into the pCR-4 Blunt-TOPO vector according to the manufacturers instruction, thereby creating plasmid pJaL617.

The amdS gene was isolated as a 2648 bp SpeI-HindII fragment from pJaL617 and cloned into the corresponding restriction sites in plasmid pJaL575, thus creating plasmid pJaL619 containing the A. oryzae amdS gene and the Herpes simples virus thymidine kinase gono (HSV TK).

Next, a 2132 bp XbaI-SalI from plasmid pJaL554 encoding the A. oryzae pyrG gene was ligated together with an 8786 bp XhoI-XbaI fragment of pJaL619 to create plasmid pJaL620, replacing a 267 bp fragment of the amdS with a 2132 bp fragment encoding the A. oryzae pyrC gene.

Then the *A. oryzae* pyrG gene was replaced with the *A. nidulans* pyrG gene by ligating the following fragments together to create the *A. oryzae* amdS deletion plasmid pMT3536:
1. The 5947 bp BssHI-XbaI DNA fragment from pJaL620;
2. The 2124 bp SpeI-NsiI DNA fragment from pHUda797; and
3. The 2798 bp NsiI-BssHI DNA fragment from pJaL620.

Plasmid pMT3536 was linearized with SpeI and used to transform *A. oryzae* COIs454 and transformants were selected on minimal medium containing 0.6 mM 5-fluoro-2'-deoxyuridine (FdU), as described in WO 0168864. A number of transformants were reisolated twice and chromosomal DNA was prepared. The chromosomal DNA from each of the transformants was digested with EcoRI and analyzed by Southern blotting, using the 705 bp $^{32}$P-labelled DNA SpeI-NheI fragment from pMT3536 containing the 5' flanks of the *A. oryzae* amdS gene as probe. Strains of interest were identified from the Southern blot by the disappearance of a 7353 bp EcoRI band and the appearance of a 9168 bp EcoRI band. One such transformant was named MT3625.

Construction of pyrG Deleted *A. oryzae* Strain, RUNG237

For removing the pyrG gene resident in the amdS gene in the *A. oryzae* strain MT3625 the following was done:

The *A. oryzae* strain MT3625 was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA. One strain, RUNG237, was identifying as being pyrG minus. RUNG237 is uridine dependent, therefore it can be transformed with the wild type pyrG gene and transformants selected by the ability to grow in the absence of uridine.

Construction of pepC-promoter Exchanged *A. oryzae* Strain, MLxN56

In *A. oryzae* strain MLxN56 its native pepC promoter was replaced by the *A. oryzae* nitratereductase promoter, PniaD, which is regulated by different nitrogen sources—the presence of nitrate will induce expression, whereas ammonium will repress expression. The promoter exchange was made in the following way:

A first 3529 bp DNA fragment containing the niaD promoter sandwiched between a 3' pepC region (part of the coding region of pepC) and a 5' partial pyrG gene was generated by SOE PCR (splicing by overlap extension PCR) as follows:
a) A 1019 bp PCR fragment was made based on chromosomal DNA of *A. oryzae* BECh2 as template with primers oJaL228 and oJaL229;
b) A 1149 bp PCR fragment was made based on chromosomal DNA of *A. oryzae* BECh2 as template with primers oJaL230 and oJaL231; and
c) A 1149 bp PCR fragment was made using plasmid pJaL554 as template with primers oJaL232 and oJaL114.

The three fragments a)-c) were purified, mixed together and a PCR reaction was carried out using primers oJaL228 and oJaL114 to generate the 3529 bp PCR fragment.

A second 2497 bp PCR fragment was generated containing a 3' partial pyrG gene and a 5' pepC region of the following two fragments amplified by PCR:
d) A 1465 bp PCR fragment was made using plasmid pJaL554 as template with primers oJaL113 and oJaL233; and
e) A 1072 bp PCR fragment was made based on chromosomal DNA of BECh2 with primers oJaL234 and oJaL235.

The two fragments d) and e) were purified and mixed together and a PCR reaction was carried out using primers oJaL113 and oJaL235 to generate the 2497 bp PCR fragment.

The first 3529 bp and the second 2497 bp PCR fragments were mixed together and transformed into *Aspergillus oryzae* RUNG237 according to the method of Christensen et al, 1988, Bio/Technology 6: 1419-1422. RUNG237 was deleted for the pyrG gene, so it can only grow on minimal medium supplemented with uridine.

Transformants were selected for their ability to grow on minimal medium, meaning that at least homologous recombination had occurred between the two PCR fragments over the 5' partial pyrG gene and 3' partial pyrG gene to generate an intact pyrG gene. Transformants were re-isolated twice. For preparation of genomic DNA the transformants were cultivated in liquid medium (2 g/l yeast extract, 2 g/l peptone peptone and 2% glucose). Chromosomal DNA was prepared as previously described in WO 0168864.

Southern analysis of the pepC locus was done with the aim to identify transformants in which a clean double cross-over between the chromosomal pepC and the 3' and 5' pepC regions of the PCR fragments had occurred. The chromosomal DNA was digested with the restriction enzymes SpeI and StuI. The Southern blot was probed with the above 1019 bp amplified PCR fragment. If the native pepC promoter had been successfully exchanged with the niaD promoter and the pyrG gene a shift in band size from 3340 bp to 6326 bp would be expected. A strain having this band shift was isolated and processed further to remove the inserted pyrG gene at the pepC locus in the following way:

The selected *A. oryzae* strain was screened for resistance to 5-flouro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodiumnitrate as nitrogen source, and 0.5 mg/ml FOA.

One such strain, MLxN56, was identified as being pyrG minus. MLxN56 has the niaD promoter operably linked with the pepC gene and it is uridine dependent, therefore it is suitable for subsequent transformation with the wild type pyrG gene and selection by the ability to grow in the absence of uridine.

Example 2

Construction of *Aspergillus* Expression Plasmids

The plasmid pCOIs1126 was cut with AfeI and AatII. The 5615 bp fragment was purified and then blunt ended with Klenow polymerase. The fragment was then ligated and the resulting plasmid was named pCOIs1150.

First a PCR fragment was amplified using pCOIs1124 as the template and using the primer pair P801 and P802. Second another PCR fragment was amplified using pCOIs1124 as the template and using the primer pair P803 and P804. The two PCR fragments were fused using SOE-PCR and the primer pair P801 and P804. The SOE-PCR fragment was inserted in pCOIs1150 linearized with PvuII using the In-Fusion kit according to the manufactory instructions. The resulting plasmid was named pCOIs1151.

A PCR fragment was amplified using pCOIs1124 as the template and using the primer pair P805 and P806. The amplified PCR fragment was In-Fusion cloned into pCOIs1151 linearized with AscI. The resulting plasmid was named pCOIs1152.

A PCR fragment was amplified using pCOIs1130 as the template and the primer pair P830 and P831. The 7532 bp HindIII-PmeI fragment from pCOIs1152 was ligated to the PCR fragment which was cut with HindIII and StuI. The resulting plasmid was named pCOIs1197.

A 9406 bp HindIII-SacII fragment from pCOIs1130 was ligated to a 1286 bp HindIII-SacII fragment from pCOIs1148. The resulting plasmid was named pCOIs1175.

A 1456 bp Tth111I-AfeI fragment from pCOIs1175 was ligated to an 8241 bp Tth111I-AfeI fragment from pCOIs1197. The resulting vector was named pCOIs1198.

The DNA sequence encoding a variant of the *Humicola lanuginose* lipase was cut with NotI and AsiSI. The resulting 947 bp fragment were ligated to the 9678 bp AsiSI-NotI fragment from pCOIs1198. The resulting plasmid was named pCOIs1202.

First, one PCR fragment was amplified using pCOIs1202 as the template and the primer pair P875 and P882. Second, another PCR fragment was amplified using pCOIs1202 as the template and the primer pair P881 and P864.

The two above PCR fragments were fused using SOE-PCR and the primer pair P875 and P864. The SOE-PCR fragment was cut with XhoI-BsiWI and ligated to an 8275 bp XhoI-BsiWI fragment from pCOIs1202. The resulting plasmid was named pCOIs1360.

A PCR fragment was amplified using pCOIs1360 as the template and the primer pair P920 and P200. The resulting PCR fragment was cut with PacI-BsrGI and the 933 bp fragment was purified and ligated to a 9512 bp PacI-BsrGI fragment from pCOIs1360. The resulting plasmid was named pCOIs1386.

First, a PCR fragment was amplified using pCOIs1386 as the template and the primer pair P921 and P922. Second, another PCR was amplified using pCOIs1386 as the template and the primer pair P923 and P924. The two PCR fragments were fused using SOE-PCR and the primer pair P921 and P924. The SOE-PCR fragment was cut with HindIII and ligated to an 8268 bp HindIII fragment from pCOIs1386 in an orientation of the fragments giving a 524 bp and a 9969 bp fragment if the resulting plasmid is cut with XhoI and ApaLI. The resulting plasmid was named pCOIs1387.

Example 3

Lipase Expression in *A. oryzae* with Native vs. niaD pepC-promoter

Construction of a *Candida antarctica* Lipase B Expression Plasmid, pMLxN31.

The *Candida antarctica* lipase B coding region was amplified by PCR with primer MLxn20 and MLxn21 from plasmid pMT1335, thus providing a 1067 bp DNA fragment. In this amplification there was added 20 bp 5' to the lipase coding region and 18 bp 3' to the lipase coding region in order to prepare it for In-Fhusion® cloning (Clontech Inc. USA). The plasmid pCOIs1198 was digested with NotI and AsiAI and the resulting 9684 bp fragment was purified from a 1% agarose gel band. The two fragments of 9684 bp and 1067 bp were mixed and spliced together by In-Fhusion® PCR. This generated an *Aspergillus* expression plasmid for the *Candida antarctica* lipase B, pMLxN31.

*Candida antarctica* Lipase B Expression in *Aspergillus oryzae* Strains

The *Aspergillus oryzae* strains RUNG237 and MLxN56 were transformed with the expression plasmid pMLxN31 as described under methods.

Shake flask containing 10 ml YPM medium (2 g/l yeast extract, 2 g/l peptone, and 2% maltose) was inoculated with spores from the generated transformants and the host BECh2 and incubated at 30° C., with shaking (200 rpm) for 4 days. Supernatants (10 µl) were analysed on SDS-page. One transformant producing the *Candida antarctica* lipase B protein from each of the parent hosts, RUNG237, and the PniaD PepC-regulated strain, MLxN56, was isolated and named MLxN69 and MLxN70, respectively.

Figure 1:
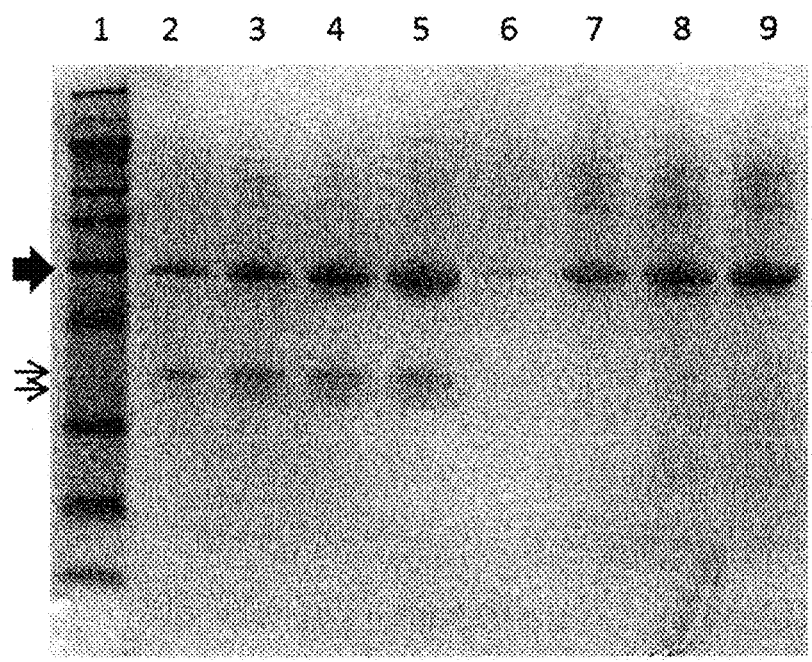
FIG. 1 shows a photo of a coomassie blue stained SDS-PAGE gel of lipase fermentation broth samples of strains MLxn69 and MLxN70. Lane 1 is the "Perfect Protein Markers™" sizes 10-225 kDa (Novagen). Lanes 2-5 are the MLxN69 samples taken on days 2-5. Lanes 6-9 are the MLxN70 samples taken on days 2-5. The bold arrow indicates the full length lipase protein; small arrows indicate degradation products of the lipase.

The MLxN69 and MLxN70 strains were fermented in 1l tanks as described under methods. FIG. 1 shows a photo of a Coomassie blue stained SDS-PAGE gel, where the product formation from the two transformants was visualised during a 5-day fermentation with samples taken daily on days 2-5. The leftmost lane in FIG. 1 is the "Perfect Protein Markers™" (Novagen) size 10-225 kDa. Lanes 2-5 show the product formation (on days 2-5) of strain MLxN69 (pepC expressed from native PepC promoter). Lanes 6-9 show the product formation (on days 2-5) of strain MLxN70 (pepC expressed from the PniaD promoter). The bold arrow in the figure indicates full length *Candida antarctica* lipase B protein. Small arrows indicate degradation products of the lipase. The protein bands were confirmed by mass spectrometry analysis to be ether the full length *Candida antarctica* lipase B protein (big arrow) or protein fragments thereof.

FIG. 1 shows that ammonia-based repression of PepC-expression (via its expression from the regulated PniaD promoter) in MLxN70 significantly reduces the degradation of the lipase, as no lipase degradation products are visible in lanes 6-9.

Stability of *Candida antarctica* Lipase B in the Fermentation Broth

Figure 2:
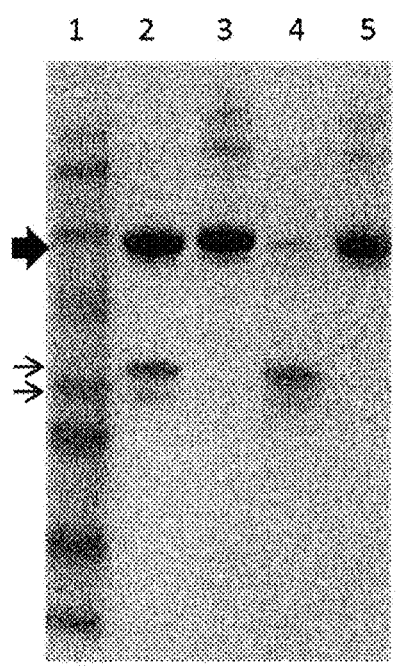
FIG. 2 shows a photo of a coomassie blue stained SDS-PAGE gel of lipase fermentation broth samples incubated at two different temperatures for the strain MLxN69 and MLxN70. Lane 1 is the "Perfect Protein Markers™" sizes 10-225 kDa (Novagen). Lanes 2 and 3 are the samples incubated at −18° C. for strains MLxn69 and MLxN70. Lanes 4 and 5 are samples incubated at 34° C. for strain MLxn69 and MLxN70.

The stability of *Candida antarctica* lipase B protein in the fermention broth from strains MLxn69 and MLxn70 was tested by incubating samples of the broth from day 5 at temperatures of −18° C. and 34° C. for 7 days. FIG. 2 shows the samples run on an SDS-PAGE gel. Lane 2 and 3 are the samples of MLxN69 and MLxN70, respectively, stored at −18° C. Lanes 4 and 5 are the samples of MLxN69 and MLxN70, respectively, stored at 34° C.

FIG. 2 shows that the lipase protein is stable in the broth of both strains when incubated at −18° C. However, incubation at 34° C. renders the lipase protein unstable in MLxN69, where the lipase protein has nearly total disappeared (lane 4). In contrast, the lipase is stable in strain MLxN70, where the expression of PepC protease is repressed via the niaD promoter (lane 5).

Example 4

Cutinase in *A. oryzae* Strains with Native vs. PniaD-regulated PepC

Construction of a *Humicola insolens* cutinase expression plasmid, pDAu689.

The *Humicola insolens* cutinase coding region was amplified by PCR with primers DAuP810 and DAuP811 to provide a 727 bp DNA fragment. In this amplification there was added 20 bp 5' to the cutinase coding region and 17 bp 3' to the cutinase coding region in order to prepare it for In-Fusion® cloning. The plasmid pCOIs1387 was digested with NotI-PvuII and the 9546 bp fragment was purified from a 1% agarose gel band. The two 9546 bp and 1067 bp PCR fragments were mixed and cloned together by In-Fusion® cloning. This generated the *Aspergillus* expression plasmid for the *Humicola insulens* cutines named pDAu689.

*Humicola insulens* Cutinase Expression in *Aspergillus oryzae* Strains

The *Aspergillus oryzae* strains RUNG237 and MLxN56 were transformed with the cutinase expression plasmid pDAu689, as described under methods.

Shake flasks containing 10 ml YPM medium (2 g/l yeast extract, 2 g/l peptone, and 2% maltose) were inoculated with spores from the generated transformants and the host BECh2 and incubated at 30° C., with shaking (200 rpm) for 4 days. Supernatants (10 μl) were analysed by SDS-PAGE. One transformant from each of the RUNG237 parent and the MLxN56 strain producing the *Humicola insulens* cutinase protein was isolated and named DAu712 and DAu729, respectively.

The two strains DAu712 and DAu729 were fermented in 1l tanks as described under methods.

Figure 4:
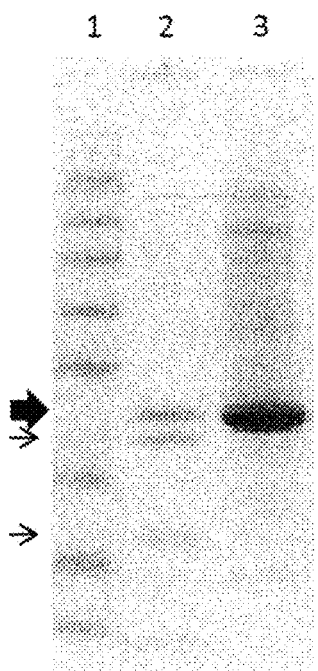
FIG. 4 shows a photo of a Coomassie blue stained SDS-PAGE gel, where the product formation at day 5 from the two transformants was visualised. The leftmost lane in FIG. 4 is the "SeeBlue Plus2™" (Invitrogen) size 4-250 kDa. Lanes 2 and 3 show the product formation on day 5 of strains DAu712 (pepC expressed from native PepC promoter) and Dau729 (pepC expressed from the PniaD promoter), respectively. The bold arrow in the figure indicates full length *Humicoli insulens* cutinase protein. Small arrows indicate degradation products of the lipase. The protein bands were confirmed by mass spectrometry analysis to be ether the full length *Humicoli insulens* cutinase protein (big arrow) or protein fragments thereof. The figure shows that ammonia-based repression of PepC-expression (via its expression from the regulated PniaD promoter) in DAu729 significantly reduces the degradation of the cutinase, as no cutinase degradation products are visible in lane 3.

FIG. 4 shows a photo of a Coomassie blue stained SDS-PAGE gel, where the product formation at day 5 from the two transformants was visualised. The leftmost lane in FIG. 4 is the "SeeBlue Plus2™" (Invitrogen) size 4-250 kDa. Lanes 2 and 3 show the product formation on day 5 of strains DAu712 (pepC expressed from native PepC promoter) and Dau729 (pepC expressed from the PniaD promoter), respectively. The bold arrow in the figure indicates full length *Humicoli insulens* cutinase protein. Small arrows indicate degradation products of the lipase. The protein bands were confirmed by mass spectrometry analysis to be ether the full length *Humicoli insulens* cutinase protein (big arrow) or protein fragments thereof. The figure shows that ammonia-based repression of PepC-expression (via its expression from the regulated PniaD promoter) in DAu729 significantly reduces the degradation of the cutinase, as no cutinase degradation products are visible in lane 3.

Example 5

Asparaginase in *A. niger* Strains with PepC vs. ΔPepC

Construction of the Expression Plasmid pHiTe50

The 1.1 kb region of *Aspergillus oryzae* asparaginase was amplified from pJN001 by PCR with primer pairs HTJP-2 and HTJP-3 containing BamHI/PmlI restriction sites based on sequence information in WO2004/032648.

SEQ ID NO: 44: Primer HTJP-2:
5' ccgcacgtgtcaagcaacccaatccgc

SEQ ID NO: 45: Primer HTJP-3:
5' cgcggatccaccatgggtgtcaatttcaaagttcttg

The obtained 1.1 kb DNA fragment containing the *Aspergillus oryzae* asparaginase gene was recovered from agarose gel and was digested with BamHI and PmlI. The BamHI-PmlI 1.1 kb fragment was ligated into the BamHI-PmlI fragment from the modified plasmid of pRika147 where its promoter was substituted with the Na2/tpi promoter used in pCols1124. The resulting plasmid was named pHiTe50. Plasmid preparation was carried out in *E. coli* DH5α. Furthermore, pHiTe50 carries the selective marker amdS from *Aspergillus nidulans*.

Transformation of an *A. niger* Parent Strain with pHiTe50

In order to express asparaginase in the *A. niger* parent strain NN059280 modifications were made in four loci targeted for integration of the asparaginase expression cassette: amyA, amyB, asaA and payA. At these loci, the asparaginase-encoding gene together with the amdS selective marker were integrated as described in WO 2012/160093. Transformants were selected from the standard medium supplemented with 10 μg/ml 5-fluorocytosine (5FC).

Randomly selected transformants were inoculated onto minimal medium plates supplemented with 10 μg/ml 5-fluorocytosine (5FC). The isolated strains were subjected to southern blotting analysis to confirm whether 4 copies of the asparaginase-encoding gene had been correctly introduced or not. The following set of primers were used to make a non-radioactive probe:

SEQ ID NO: 46: Primer HTJP-24:
5' ccgcaacaacaggttacaaag

SEQ ID NO: 47: Primer HTJP-25:
5' ccaggttacccatttcgatg

Chromosomal DNA extracted from the selected transformants was digested by HindIII. By the right gene disruption event, hybridized signals at the sizes of 7.8, 4.7, 6.4 and 4.4 kb at amyA, amyB, asaA and payA loci were confirmed with the probe. One 4-copy asparaginase strain denoted 50-4C-9 was selected.

Transformation of PepC-deficient *A. niger* Progeny Strain with pHiTe50

In order to express asparaginase in the PepC-deficient C2948 strain (a derivative of the parent NN059280) modifications were made in four loci targeted for integration of the asparaginase expression cassette: amyA, amyB, asaA and payA. At these loci, the asparaginase-encoding gene together with the amdS selective marker were integrated as described in WO 2012/160093. Transformants were selected from the standard medium supplemented with 10 μg/ml 5-fluorocytosine (5FC).

Randomly selected transformants were inoculated onto minimal medium plates supplemented with 10 μg/ml 5-fluorocytosine (5FC). The isolated strains were subjected to southern blotting analysis to confirm whether 4 copies of the asparaginase-encoding gene had been correctly introduced or not.

Chromosomal DNA extracted from the selected transformants was digested by HindIII. By the right gene disruption event, hybridized signals at the sizes of 7.8, 4.7, 6.4 and 4.4 kb at amyA, amyB, asaA and payA loci were confirmed with the probe. One 4-copy asparaginase strain denoted 50-C2948-9 was selected.

Asparaginase Expression in *A. niger* Strains 50-4C-9 (PepC+) vs. 50-C2948-9 (ΔPepC)

The asparaginase activities of the supernatants of strains 50-4C-9 (native PepC) vs. 50-C2948-9 (ΔPepC) were determined. The two strains were tank-fermented in parallel under the standard *A. niger* fermentation conditions at pH 4.75, where asparaginase is usually degraded by PepC activity. The asparaginase activities (rASNU) were measured as follows:

The asparaginase assay method utilizes the hydroxylaminolysis reaction of asparaginase in which transamidation occurs between asparagine and hydroxylamine (Dunlop et al (1980) Reactions of asparaginase II of *Saccharomyces cerevisiae*. A mechanistic analysis of hydrolysis and hydroxylaminolysis. Journal of Biological Chemistry, 255(4), p. 1542-1546).

The reaction product, β-aspartohydroxamate, forms the red-colored ferric hydroxamate complex with FeCl$_2$, which can be read at A490. A good linearity of the standard curve with KSF0083 was observed in the range of 0-8ASNU/ml.

The Protocol for Asparaginase Assay in 96 Well Plate (rASNU Assay)

Reagent:
1M Potassium phosphate buffer (pH6.0)
1M KH$_2$PO$_4$ (136 g/500 ml)+1M K$_2$HPO$_4$ (174 g/500 ml)
Adjust to pH6.0
100 mM Potassium phosphate buffer (pH6.0)+0.1% tritonX-100 (1 L)
  100 ml 1M Potassium phosphate buffer (pH6.0)
  1 g Triton X-100
  Adjust to 1000 ml
2M Hydroxylamine (HA) solution (100 ml)
  13.9 g hydroxylamine
  Adjust to 100 ml with 100 mM potassium phosphate buffer (pH6)
Stop solution (500 ml)
  23.83 ml acetate
  13.88 g FeCl$_3$ 6H$_2$O
  84 ml 5N HCl
  Adjust to 500 ml with H$_2$O
Substrate solution (100 ml)
  10 ml 1M Potassium phosphate buffer
  0.5 g L-asparagine (132.12, final conc. 0.0325M)
  5 ml 2M HA soln.
  Adjust to 100 ml with H$_2$O.
Standard (KSF0083: 14280ASNU/g) 100ASNU/ml solution
  0.7002 g/100 ml 100 mM Potassium phosphate buffer (pH6)+0.1% tritonX-100
  (0.3501 g/50 ml, 0.1751 g/25 ml, 0.07 g/10 ml)

The asparaginase assay results are shown in table 1 below, wherein the rASNU activity from strain 50-4C-9 is normalized to 1.00.

TABLE 1

Asparaginase activity from *A. niger* strains w/o PepC activity.

| Strain | Plasmid | PepC | Relative asparaginase activity |
|---|---|---|---|
| 50-4C-9 | pHiTe50 | Native | 1.00 |
| 50-C2948-9 | pHiTe50 | ΔPepC | 4.88 |

Figure 3:
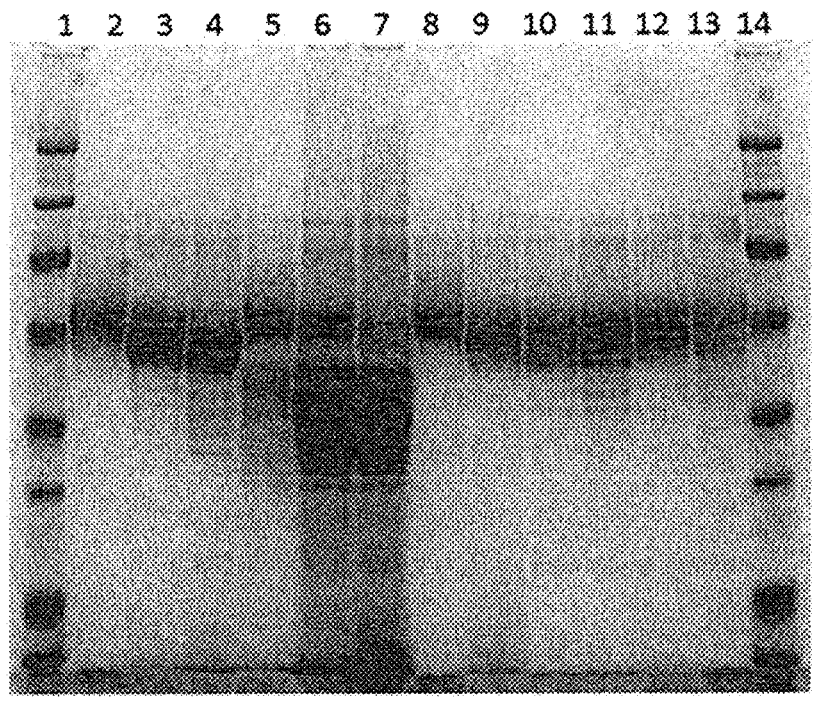
FIG. 3 shows a photo of a coomassie blue stained SDS-PAGE gel of fermentation broth samples from Examples 5 and 6 at 96, 144 and 190 hrs showing asparaginase expressed in strains where pepC was regulated by the sorA- or sorb promoters. Lane1: Molecular marker (Biorad #161-0318); Lanes 2-4: Strain 50-C2948-9 (ΔPepC); Lanes 5-7: Strain 50-4C-9 (native PepC); Lanes 8-10: Strain 91-50-C2948-18 (PsorA-pepC); Lanes 11-13: Strain 92-50-C2948-13 (PsorB-pepC); Lane14; Molecular marker.

The fermentation samples from the two *A. niger* strains 50-4C-9 (native PepC) and 50-C2948-9 (ΔPepC) were also subjected to SDS-PAGE analysis to see and compare the degree of degradation of the asparaginase. As anticipated, the samples from 50-4C-9 were severely degraded in the presence of PepC (FIG. 3, lanes 5-7), whereas the asparaginase expressed in 50-C2948-9 (ΔPepC) was considerably more stable (FIG. 3, lanes 2-4).

However, even though the stability of the asparaginase in the PepC-inactivated strain was much improved compared with the PepC wildtype strain, there is a drawback. Inactivation of PepC is known to reduce sporulation and growth rate significantly, as previously described for *Aspergillus fumigatus* (Reichard U et al. 2000, Int J Med Microbiol. 290, 549-558). It is important to retain the ability of industrial protein production host cells to form spores on solid medium; spores are required for industrial cell-bank preparation, so that successful future tank-inoculations are secured in industrial-scale protein production.

Example 6

Asparaginase in *A. niger* Strains with Native vs. PsorA/sorB-Regulated PepC

Construction of the Plasmids pHiTe91 and pHiTe92

The primers for the promoter sequence of the sorA and sorB genes were designed based on the genome sequences information in *Aspergillus oryzae* RIB40 (ATCC 42149). The 1.4 kb region of the sorA was amplified by PCR with primer pairs, HTJP-231 and HTJP-233 using genomic DNA of *A. oryzae* RIB40 as template. The 2.3 kb region of the pepC gene and terminator were amplified by PCR with primer pairs, HTJP-232 and HTJP-234 using genomic DNA of *A. niger* NN059280 (WO 2012/160093) as template.

The 3.7 kb region of sorA promoter with pepC and its terminator was amplified by PCR with primer pairs, HTJP-231 and HTJP-232. The amplified 3.7 kb fragment was inserted into the pHUda801 at SpeI site via In-Fusion® PCR Cloning System (Clontech) to create an intermediate plasmid pHiTe82. Plasmid preparation was carried out in *E. coli* DH5α.

Primers for pepC and sorA Promoter:

```
SEQ ID NO: 48: HTJP-231
ctaactactaactaggttaattaactccccgaccaccaagttcc

SEQ ID NO: 49: HTJP-232
aaaatactttactagtgcatgcatgaggtcttttg

SEQ ID NO: 50: HTJP-233
gcccttcatggtggctagcttcggtgcactaatagtatgac

SEQ ID NO: 51: HTJP-234
gtgcaccgaagctagccaccatgaagggcatcctcggcc
```

The 0.6 kb region of sorB promoter was amplified by PCR with primer pairs, HTJP-235 and HTJP-236 using genomic DNA of *A. oryzae* RIB40 as template. The obtained 0.6 kb DNA fragment containing the sorB promoter was recovered from agarose gel. The 0.6 kb amplified DNA fragment was digested with PacI and NheI, ligated into the pHiTe82 digested with PacI and NheI to create an intermediate plasmid pHiTe83. Plasmid preparation was carried out in *E. coli* DH5α.

Primers for pepC and sorB Promoter:

```
SEQ ID NO: 52: HTJP-235
ccttaattaagacgcagtgtccctgtatta

SEQ ID NO: 53: HTJP-236
ctagctagctttgctccctaaactctaaac
```

The 3.7 kb fragment of the sorB promoter-pepC and its terminator was amplified by PCR with primer pairs, HTJP-280 and HTJP-281 using the plasmid pHiTe82. The amplified fragments were integrated in the pHUda1306 at NheI site by In-Fusion® cloning. The resulting plasmid was named pHiTe91. This plasmid also comprised the selective marker pyrG from *Aspergillus nidulans*.

Primers for Promoter sorA-pepC:

```
SEQ ID NO: 54: HTJP-280
agttaattaagctagcctccccgaccaccaagttc

SEQ ID NO: 55: HTJP-281
gtaagactgagctagcgcatgcatgaggtcttttg
```

The 2.9 kb fragment of sorB promoter-pepC and the pepC terminator was amplified by PCR with primer pairs, HTJP-281 and HTJP-282 using the plasmid pHiTe83. The amplified fragments were integrated in the pHUda1306 at NheI site by In-Fusion. The resulting plasmids were termed as pHiTe92. Furthermore, these plasmids comprised the selective marker pyrG from *Aspergillus nidulans*.

Primers for Promoter sorB-pepC:

```
SEQ ID NO: 55: HTJP-281
gtaagactgagctagcgcatgcatgaggtcttttg

SEQ ID NO: 56: HTJP-282
agttaattaagctagcgacgcagtgtccctg
```

Asparaginase in *A. niger* Strain (ΔPepC) C2948-6

*Aspergillus niger* strain C2948 is a pepC gene deficient derivative of NN059280. The pyrG gene rescue of C2948 was performed to generate C2948-6 (as described in WO 2012/160093).

Chromosomal insertion into *A. niger* C2948-6 of the asparaginase gene with amdS selective marker (pHiTe50) and the PsorA- or PsorB-regulated pepC gene with pyrG marker (pHiTe91 or pHiTe92, respectively) was performed as described in WO 2012/160093.

Transformants were selected from the standard medium supplemented with 10 μg/ml 5-fluorocytosine (5FC). Randomly selected transformants were inoculated onto the minimal medium plates supplemented with 10 μg/ml 5FC. Strains which grew well were purified and subjected to southern blotting analysis to select strains with identical copy number of each gene.

Genomic DNA extracted from the selected transformants was digested by HindIII. Among the strains given the right integration events, 91-50-C2948-18 (3-copy asparaginase and 1-copy sorA-promoter-pepC) and 92-50-C2948-13 (3-copy asparaginase and 1-copy sorB-promoter-pepC) were selected.

Sporulation on COVE-N-gly by Sorbitol Inducible Promoters

The isolated strains were also evaluated by their sporulation ability on COVE-N-gly (sorbitol) agar medium. As mentioned above, disruption of pepC gene causes significant reduction of regular sporulation and growth rate as previously described for *Aspergillus fumigutus* (Reichard U et al. 2000, Int J Med Microbiol. 290, 549-558). It is important to retain the pepC activity until the cells completely forms spores on the solid medium since sufficient number of spores is required for inoculation at industrial-scale protein production. Thus, isolated strains were evaluated by their sporulation ability on the COVE-N-gly (sorbitol) slant. As shown in the Table 2, spore-yields of the strains where the pepC gene is regulated by PsorA or PsorB were significantly higher compared to the pepC deficient strain, suggesting sporulation induction can be achieved by conditional expression of PepC with the sorA/B promoters.

TABLE 2

Spore yield in PepC-deficient and PepC conditional expression strains.

| Strain | PepC | Number of spores/slant (mean values are shown: n = 3) |
|---|---|---|
| 50-4C-9 | wildtype | 5.33E+07 |
| 50-C2948-9 | ΔpepC | 3.73E+06 |
| 91-50-C2948-18 | PsorA-pepC | 2.77E+07 |
| 92-50-C2948-13 | PsorB-pepC | 4.48E+07 |

Regulation of PepC Expression by sorA and sorB Promoters

To confirm if the PepC expression can be down-regulated in the absence of sorbitol, the asparaginase activities of the strains 91-50-C2948-18 (sorA-promoter-pepC) and 92-50-C2948-13 (sorB-promoter-pepC) were evaluated by lab-scale tanks. The asparaginase activity of the supernatants of each transformant was determined. As a reference, 50-4C-9 and 50-C2948-9 (see above) were fermented in parallel under the standard *A. niger* fermentation conditions at pH 4.75 where asparaginase is degraded by PepC. The asparaginase activities (rASNU activities) were measured followed by the methods described above; results are shown in table 3 below, wherein the asparaginase (rASNU) activity from strain 50-4C-9 is normalized to 1.00.

TABLE 3

Asparaginase activity from *A. niger* strains with native and regulated PepC expression.

| Strain | Plasmid | PepC | Relative asparaginase activity |
|---|---|---|---|
| 50-4C-9 | pHiTe50 | Native | 1.00 |
| 91-50-C2948-18 | pHiTe50&pHITe91 | PsorA | 4.34 |
| 92-50-C2948-13 | pHiTe50&pHITe92 | PsorB | 4.00 |

The fermentation samples from the *A. niger* strains in Examples 5 and 6 were subjected to SDS-PAGE analysis to see and compare the degree of degradation of the asparaginase. As anticipated, the samples from 50-4C-9 (native PepC) were severely degraded in the presence of PepC (FIG. 3, lanes 5-7), whereas the asparaginase expressed in 50-C2948-9 (ΔPepC) was considerably more stable (FIG. 3, lanes 2-4). The degradation in the samples from strains 91-50-C2948-18 and 92-50-C2948-13 also showed significantly less degradation of asparaginase (FIG. 3, lanes 8-13), suggesting that PepC expression was strongly repressed by the sorA- and sorB promoters under the tank fermentation conditions.

Example 7

Asparaginase in *A. niger* Strains with Native vs. PniaD-regulated PepC

Construction of the Plasmids pHiTe106 and pHiTe107

The 1.4 kb region of niaD promoter was amplified by PCR with primer pairs, HTJP-341 and HTJP-342 using genomic DNA of *A. oryzae* Bech2 as template. The obtained 1.4 kb DNA fragment containing the niaD promoter was recovered from agarose gel. The 1.4 kb amplified DNA fragment was digested with PacI and NheI, ligated into the pHiTe82 digested with PacI and NheI to create an intermediate plasmid pHiTe106. Plasmid preparation was carried out in *E. coli* DH5α.

Primers for niaD Promoter:

SEQ ID NO: 57: HTJP-341
ccttaattaaggatgtggacgggttatcg

SEQ ID NO: 58: HTJP-342
ctagctagcgttaccggcagggaagg

The 3.7 kb PacI-SpeI digested fragment (niaD promoter-pepC and the pepC terminator) from pHiTe106 was ligated with the 7.6 kb PacI-NheI fragment from pHiTe91 to create the plasmid pHiTe107. Furthermore, these plasmids comprised the selective marker pyrG from *Aspergillus nidulans*.

Asparaginase in *A. niger* Strain (ΔPepC) C2948-6

*Aspergillus niger* strain C2948 is a pepC gene deficient derivative of NN059280. The pyrG gene rescue of C2948 was performed to generate C2948-6 (as described in WO 2012/160093).

Chromosomal insertion into *A. niger* C2948-6 of the asparaginase gene with amdS selective marker (pHiTe50) and the PniaD-regulated pepC gene with pyrG marker (pHiTe107) was performed as described in WO 2012/160093.

Transformants were selected from the standard medium supplemented with 10 μg/ml 5-fluorocytosine (5FC). Randomly selected transformants were inoculated onto the minimal medium plates supplemented with 10 μg/ml 5FC. Strains which grew well were purified and subjected to southern blotting analysis to select strains with identical copy number of each gene.

Genomic DNA extracted from the selected transformants was digested by Among the strains given the right integration events, 107-C2948-20 (3-copy asparaginase and 1-copy niaD-promoter-pepC) was selected.

Isolated strains were evaluated by their sporulation ability on the COVE-N-gly slant. As shown in the Table 4, spore-yields of the strains where the pepC gene is regulated by PniaD were also significantly higher compared to the pepC deficient strain, showing that sporulation induction can be achieved by conditional expression of pepC with the niaD promoter.

TABLE 5

Asparaginase activity from *A. niger* strains with native and regulated PepC expression.

| Strain | Plasmid | PepC | Relative asparaginase activity |
|---|---|---|---|
| 50-4C-9 | pHiTe50 | Native | 1.00 |
| 107-C2948-20 | pHiTe50&pHITe107 | PniaD | 4.07 |

Regulation of PepC Expression by niaD Promoter

To confirm if the PepC expression can be down-regulated in the presence of ammonium, the asparaginase activities of the strains 107-02948-20 (PniaD-pepC) was evaluated by lab-scale tanks. The asparaginase activity of the supernatants of the transformant was determined. As a reference, 50-4C-9 and 50-C2948-9 (see above) were fermented in parallel under the standard *A. niger* fermentation conditions at pH 4.75 where asparaginase is degraded by PepC. The asparaginase activities (rASNU activities) were measured followed by the methods described above; results are shown in table 5 below, wherein the asparaginase (rASNU) activity from strain 50-4C-9 is normalized to 1.00.

TABLE 4

Spore yield in pepC deficient and pepC gene-conditional expression strains.

| Strain | PepC | Number of spores/slant (mean values are shown: n = 3) |
|---|---|---|
| 50-4C-9 | wildtype | 5.33E+07 |
| 50-C2948-9 | ΔpepC | 3.73E+06 |
| 107-C2948-20 | PniaD-pepC | 4.48E+07 |

The fermentation samples from the *A. niger* strains in Examples 7 were subjected to SDS-PAGE analysis to see and compare the degree of degradation of the asparaginase. As anticipated, the samples from 50-4C-9 (native PepC) were severely degraded in the presence of PepC (FIG. 5, lanes 5-7), whereas the asparaginase expressed in 50-C2948-9 (ΔPepC) was considerably more stable (FIG. 5, lanes 8-10). The degradation in the samples from strains 107-C2948-20 also showed significantly less degradation of asparaginase (FIG. 5, lanes 2-4, suggesting that PepC expression was strongly repressed by the niaD promoter under the tank fermentation conditions.

The invention claimed is:

1. A recombinant fungal host cell comprising:
   (a) at least one first polynucleotide encoding a polypeptide of interest; and
   (b) one or more second polynucleotides encoding a fungal PepC protease, wherein the one or more second polynucleotides are operably linked to a regulated heterologous promoter, wherein the regulated heterologous promoter is induced in the presence of nitrate and repressed in the presence of ammonium, or wherein the regulated heterologous promoter is induced in the presence of sorbitol and repressed in the absence of sorbitol, and wherein expression of the fungal PepC protease under control of the regulated heterologous promoter in the recombinant fungal host cell (1) reduces degradation of the polypeptide of interest compared to expression of PepC under control of the native promoter, (2) increases spore yield of the recombinant fungal host cell compared to a fungal host cell having the PepC protease-encoding gene deleted; and (3) increases activity of the polypeptide of interest.

2. The host cell of claim 1, which is a filamentous fungal host cell.

3. The host cell of claim 2, wherein the filamentous fungal host cell is selected from the group consisting of an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium suiphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phiebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* and *Trichoderma viride* cell.

4. The host cell of claim 1, wherein the at least one first polynucleotide is present in the chromosome of the host cell.

5. The host cell of claim 4, wherein the at least one first polynucleotide is present in the chromosome of the host cell in two or more copies.

6. The host cell of claim 1, wherein the polypeptide of interest is an enzyme selected from the group consisting of a hydrolase, an isomerase, a ligase, a lyase, an oxidoreductase and a transferase.

7. The host cell of claim 6, wherein the polypeptide of interest is an enzyme selected from the group consisting of an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, and xylanase.

8. The host cell of claim 1, wherein the PepC protease is selected from the group consisting of:
(a) a polypeptide comprising an amino acid sequence having at least 95% sequence identity to the mature sequence shown in positions 1 to 380 of SEQ ID NO: 2 or in positions 1 to 418 of SEQ ID NO: 4;
(b) a polypeptide encoded by a polynucleotide comprising a nucleotide sequence having at least 95% sequence identity to the mature polypeptide coding sequence of SEQ ID NO: 1 or SEQ ID NO: 3; and
(c) a fragment of the polypeptide of (a) or (b) that has protease activity.

9. The host cell of claim 1, wherein the PepC protease is expressed with a pro-peptide comprising an amino acid sequence shown in positions −99 to −1 of SEQ ID NO: 2 or in positions −99 to −1 of SEQ ID NO: 4.

10. The host cell of claim 1, wherein the PepC protease is expressed with a signal-peptide comprising an amino acid sequence shown in positions −115 to −100 of SEQ ID NO: 2 or in positions −115 to −100 of SEQ ID NO: 4.

11. The host cell of claim 1, wherein the regulated heterologous promoter is induced in the presence of nitrate and repressed in the presence of ammonium.

12. The host cell of claim 1, wherein the regulated heterologous promoter is induced in the presence of sorbitol and repressed in the absence of sorbitol.

13. A method of producing a polypeptide of interest, said method comprising the steps of:
(a) cultivating the host cell of claim 1, under conditions for the production of the polypeptide of interest; and, optionally
(b) recovering the polypeptide of interest.

14. The fungal host cell of claim 2, wherein the filamentous fungal host cell is selected from the group consisting of an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phiebia, Piromyces, Pleurotus, Schizophyllum, Talaromyces, Thermoascus, Thielavia, Tolypocladium, Trametes,* and *Trichoderma* cell.

15. The host cell of claim 11, wherein the regulated heterologous promoter is a filamentous fungal nitrate reductase promoter.

16. The host cell of claim 15, wherein the filamentous fungal nitrate reductase promoter is from an *Aspergillus* or a *Trichoderma* cell.

17. The host cell of claim 15, wherein the filamentous fungal nitrate reductase promoter is from an *Aspergillus niger, Aspergillus oryzae* or *Trichoderma reesei* cell.

18. The host cell of claim 15, wherein the nitrate reductase promoter is the niaD nitrate reductase promoter from *Aspergillus niger, Aspergillus oryzae* or *Trichoderma reesei*.

19. The host cell of claim 12, wherein the regulated heterologous promoter is a filamentous fungal sorbitol transporter promoter or a sorbitol dehydrogenase promoter.

20. The host cell of claim 19, wherein the filamentous fungal sorbitol transporter promoter or the sorbitol dehydrogenase promoter is from an *Aspergillus* or *Trichoderma* cell.

21. The host cell of claim 19, wherein the filamentous fungal sorbitol transporter promoter or the sorbitol dehydrogenase promoter is from *Aspergillus niger, Aspergillus oryzae,* or *Trichoderma reesei*.

22. The host cell of claim 19, wherein the filamentous fungal sorbitol transporter promoter or the sorbitol dehydrogenase promoter is the sorA or the sorb promoter from *Aspergillus niger, Aspergillus oryzae,* or *Trichoderma reesei*.

23. The host cell of claim 8, wherein the PepC protease comprises an amino acid sequence having at least 95% sequence identity to the mature sequence shown in positions 1 to 380 of SEQ ID NO: 2 or in positions 1 to 418 of SEQ ID NO: 4.

24. The host cell of claim 8, wherein the PepC protease comprises the mature sequence shown in positions 1 to 380 of SEQ ID NO: 2 or in positions 1 to 418 of SEQ ID NO: 4.

25. The host cell of claim 11, wherein the regulated heterologous promoter comprises the nucleotide sequence of SEQ ID NO: 41.

26. The host cell of claim 12, wherein the regulated heterologous promoter comprises the nucleotide sequence of SEQ ID NO: 42 or SEQ ID NO: 43.

* * * * *